(12) United States Patent
van den Brink et al.

(10) Patent No.: US 7,625,526 B2
(45) Date of Patent: Dec. 1, 2009

(54) REACTOR ASSEMBLY

(75) Inventors: Peter John van den Brink, Driebergen (NL); Maarten Bracht, Amsterdam (NL); Gerardus Johannes Maria Gruter, Heemstede (NL); Rene de Ruiter, Enkhuizen (NL); Bashir Husein Harji, Cottenham (GB)

(73) Assignee: Avantium International B.V., Amsterdam (NL)

( * ) Notice: Subject to any disclaimer, the term of this patent is extended or adjusted under 35 U.S.C. 154(b) by 929 days.

(21) Appl. No.: 10/477,028

(22) PCT Filed: May 13, 2002

(86) PCT No.: PCT/EP02/05322

§ 371 (c)(1),
(2), (4) Date: Apr. 23, 2004

(87) PCT Pub. No.: WO02/092220

PCT Pub. Date: Nov. 21, 2002

(65) Prior Publication Data

US 2004/0202573 A1    Oct. 14, 2004

(30) Foreign Application Priority Data

May 11, 2001    (EP) .................................. 01201739

(51) Int. Cl.
*B01J 19/00* (2006.01)
*B01J 10/00* (2006.01)
*G01N 15/06* (2006.01)

(52) U.S. Cl. ........................ 422/130; 422/129; 422/68.1

(58) Field of Classification Search ................ 422/68.1, 422/129, 130, 211
See application file for complete search history.

(56) References Cited

U.S. PATENT DOCUMENTS 3,615,235 A * 10/1971 Hrdina ........................ 422/70
4,787,988 A    11/1988 Bertoncini et al.
5,266,270 A    11/1993 Ajot et al.

(Continued)

FOREIGN PATENT DOCUMENTS

EP    1 065 504 A1    1/2001

(Continued)

OTHER PUBLICATIONS

Randhava, R.; Advanced Configurations for Catalyst Research; Chemical Engineering Process, American Institute of Chemical Engineers, New York, US vol. 70, No. 11, Nov. 1983; pp. 52-58; XP-000929492; col. 1, Figure 5.

*Primary Examiner*—Walter D Griffin
*Assistant Examiner*—Lessanework Seifu
(74) *Attorney, Agent, or Firm*—Hoffmann & Baron, LLP

(57) ABSTRACT

A reactor assembly for analysing the effluent stream from at least one flow-through reactor, The reactor includes a flow-through reactor for performing at least one chemical reaction. The flow-through reactor includes a reaction chamber including a reaction zone, the reaction chamber being connected to a reactor inlet for a reactant, upstream of the reaction zone and a reactor outlet for the effluent stream from the reaction zone, downstream of the reaction zone; and an analyser for subjecting the effluent stream to an analysing procedure, each reactor outlet being connected to an analyser by an effluent conduit. The reactor assembly further includes a dilution fluid supply member for adding a dilution fluid to the effluent stream, downstream of the reaction zone.

7 Claims, 14 Drawing Sheets

U.S. PATENT DOCUMENTS

| | | | |
|---|---|---|---|
| 5,714,127 A | 2/1998 | DeWitt et al. | |
| 6,069,012 A | 5/2000 | Kayser | |
| 6,149,882 A * | 11/2000 | Guan et al. | 422/211 |
| 6,548,305 B1 * | 4/2003 | Deves et al. | 436/37 |
| 6,766,817 B2 | 7/2004 | da Silva | |

FOREIGN PATENT DOCUMENTS

| | | |
|---|---|---|
| EP | 1 108 467 A2 | 6/2001 |
| WO | WO 97/09353 | 3/1997 |
| WO | WO 99/60396 | 11/1999 |
| WO | WO 99/64160 | 12/1999 |

* cited by examiner

REACTOR ASSEMBLY

FIELD OF THE INVENTION

The invention relates to a reactor assembly for analysing the effluent stream from at least one flow-through reactor. The invention further relates to a process for analysing a fluid effluent stream from a flow-through reactor.

BACKGROUND OF THE INVENTION

Reactor assemblies are known in the art for e.g. testing optimal reaction conditions for chemical reactions, including biological and pharmacological processes, such as testing the pharmacological activity of a test compound, the activity of a catalyst or enzyme, optimal reaction parameters etc. E.g. WO 99/64160 (herein incorporated by reference) describes a reactor assembly of the above-mentioned kind for testing and/or screening a collection of compounds in order to find the optimal reaction conditions and performance of the said compounds. As the reactor assembly is designed for testing and or screening purposes and not for production purposes, the reactor outlets are connected to an analyser, wherein the effluent stream from the reactor is analysed.

In practice, many different analysers are used for testing and/or screening purposes, such as a gas chromatograph (GC), chromatography devices, such as chromatography columns, in particular high-performance liquid chromatography (HPLC), optical defraction measuring devices, mass spectrograph, etc.

For testing and/or screening purposes, the reactor assemblies are chosen to be as small as possible in size in view of saving material to be tested, energy, etc. However, numerous problems often occur when using reactor assemblies known in the art. When e.g. the composition of a reaction mixture is to be analysed, the composition of the effluent of the reaction zone is analysed and compared to the composition of the stream entering the reaction zone, e.g. after and before the reaction, respectively. To accurately assess the reaction performance, e.g. the exact mass balance of the in- and outgoing components are to be calculated. Especially when analysing a small amount of effluent stream, in particular when operating with a liquid flow rate of less than 1.0 ml/min/reactor, in particular less than 0.5 ml/min, and/or a gas flow rate of less than 100 Nml/min/reactor, in particular less than 50 Nml/min/reactor as is often the case in so called high-throughput experimentation as described in WO 99/64160, it has been proven to be very difficult to analyse the composition of the effluent stream in an accurate manner. The term "Nml" means the volume of the gas at 1 atm and 20° C. The accuracy of the analyses tends to be more difficult when smaller amounts of effluent stream are available for analyses. It has e.g. been found that a significant amount of effluent stream may remain in the reaction chamber, e.g. due to adhesion of one or more of the components, present in the effluent stream, to the wall of the reaction chamber, leading to measurement inaccuracies. Further this may also cause an undesired time delay between the moment the efficient stream leaves the reaction zone and the moment the reactants of the said steam arrive at an analyser, which is highly undesired for high-throughput experimentation. Further, it is not possible to conduct accurate measurements on e.g. concentration, fluxes and production rate when a small amount of effluent stream is available for analyses.

A particular problem occurs when dealing with gas/liquid mixtures exiting the reactor, especially when dealing with the low flow rates as mentioned above. Gas/liquid separation, which is essential for subsequent analysis of both phases, is very difficult on the small flows to be separated. The reason behind this is the fact that a gas liquid separator for these small flows has to be small as well to avoid unnecessary hold-up of the products to be analysed. The small dimensions of such G/L separators will cause adhesive forces such as capillary force and surface tension effects to dominate over gravity, and as such will hinder easy separation based on gravity.

OBJECTS OF THE INVENTION

The main object of the invention is to provide a solution to one or more of the above and other problems and, among other things, to provide a reactor assembly for ensuring that substantially the whole effluent stream can be diluted and prepared for analysis, especially when operating with a liquid flow regime of less than 1.0 ml/min, in particular less than 0.5 ml/min, and/or a gas flow rate of less 100 Nml/min/reactor, preferably less than 50 Nml/min/reactor.

SUMMARY OF THE INVENTION

The invention provides reactor assembly having at least one dilution fluid supply means, for adding at least one dilution fluid to the effluent stream, downstream of the reaction zone.

By providing dilution fluid supply means, dilution fluid can be added to the effluent stream, therewith diluting the components of the effluent stream in the dilution fluid, so that sufficient volume, comprising the components of the effluent stream, for accurate analyses procedures as e.g. indicated above is provided.

As indicated above, the reaction chamber accommodates the reaction zone, wherein the chemical reaction takes place. It is to be noted that the chamber may also comprise a first space upstream of the reaction zone, e.g. to allow proper mixing and/or evaporation of reactants, entering the reaction chamber from one or more reactor inlets. In the said space, one ore more mixing devices may be present. Further, the reaction chamber may, in presence or absence of the said first space, comprise a second space downstream of the reaction zone, for receiving the reaction mixture, passing the reaction zone. However, it is also possible that the reaction zone occupies the complete reaction chamber.

It is preferred that the complete effluent stream is diluted with the dilution fluid; thereto, the dilution fluid supply means are designed such, that the whole effluent stream leaving the reaction zone receives dilution fluid; the skilled person will be aware of proper positioning of the dilution fluid supply means to dilute the said whole effluent stream. It is particularly preferred that the dilution supply means discharge in the reaction chamber, downstream of the reaction zone.

In a preferred embodiment, when the reaction chamber comprises a second space, downstream of the reaction zone as described above, the dilution fluid supply means discharge in the reaction chamber, downstream of the reaction zone, e.g. in the said second space. By such an arrangement, the dilution fluid is contacted with the complete effluent stream, comprising the reaction mixture, ensuring proper dilution of the said complete reaction mixture.

It is preferred to contact the effluent stream with the dilution fluid directly after leaving of the effluent stream from the reaction zone. Thereto the dilution fluid supply means preferably discharge in the vicinity of the downstream end of the reaction zone, preferably such that the dilution fluid contacts the said downstream end, so that any loss or delay of components from the reaction mixture is minimised.

In another embodiment, the dilution fluid supply means are connected to each of the effluent conduits. The reaction chamber can comprise one or more effluent conduits, each being connected to at least one analyser. As it is preferred to analyse the effluent in each analyser in diluted form, each of the effluent conduits are capable to receive dilution supply means. However, it may also be possible with the assembly according to the invention to provide dilution fluid to one or more effluent conduits, while other effluent conduits are present, wherethrough a portion of the effluent stream is transported, e.g. to an analyser, in undiluted form. With the assembly it will also be able to dose more than one diluent fluid to the reactor outlet or effluent conduit(s). The addition of such a multitude of fluids will allow dilution of the reaction products in one of the diluents. Typically the multitude of diluents will be mutually immiscible and form separate phases when coming together, such as for example a gas and a liquid phase. Also two immiscible liquid diluents may be added.

Each reactor preferably has a single reactor outlet, for passing through the complete effluent stream. In this case, a single effluent conduit is connected to the said outlet. Thus, the complete effluent stream is transported through the said single effluent conduit, to one or more analysers. In such an arrangement, it is sufficient for the dilution fluid supply means to be connected to the said single effluent conduit, enabling simple design of the reactor assembly. It is to be understood however, that once the effluent stream is diluted, the effluent conduit, downstream of the entry of the dilution fluid, may be branched, wherein the conduit branchs can be connected to a plurality of different analysers. Also, one or more of the said conduit branches can be connected to storage or waist vessels in order to respectively store the diluted reaction mixture for later analyses, or to discharge the respective portion of the deluted reaction products.

To get a proper mixing between the effluent and the dilutent a mixing system may be placed downstream from the location where the dilution fluid supply means discharge in the reaction chamber or the effluent conduit(s). Also a buffer vessel may be present to dampen fluctuations in concentrations that may be caused due to fluctuations in the flow of the effluent exiting the reactor.

Preferably, the reaction zone comprises a fixed catalyst bed. The fixed catalyst bed will at least be part of, or define the reaction zone, when the reaction process requires the action of the catalyst in the bed. By the fixed bed arrangement, a well-defined reaction zone (the bed) is present in the reaction chamber, enabling accurate and optimal positioning of the discharge end of the dilution supply means within the reaction chamber, i.e. in the vicinity of the downstream end of the catalyst bed to enable direct dilution of the reaction mixture after leaving the said catalyst bed. Further, fixed catalyst beds are extremely well suited for testing of or screening for the activity of a catalyst. Preferred is a fixed catalyst bed operating in downflow operation mode where either or both liquid and gas are following the direction of gravity. However, also other fixed bed reactor operation mode can be used, such as, counter current, horizontal flow or co-current upflow operation mode. Instead of a fixed catalyst bed also fluidised bed, ebullating bed, continuously stirred tank reactor or a bubble column can be used. In the reaction zone various types of reactions can be performed, such as, oxidation reactions, hydrogenation reactions, condensation reactions, hydration reactions, de-hydration reactions and cracking reactions. These reactions may be carried out in the gas phase, in the liquid phase, or in multi-phase where both gas and liquid reactants are brought in the reaction zone. In case a catalyst is present in the reaction zone it may be in the form of e.g. grains (sieve fraction), flakes, balls, monoliths or fibres. The catalyst bed can be supported by a frit, a quarts wool plug or a filter plate. Those who are skilled in the art will understand that many more variations can be made to the above mentioned descriptions of the reaction zone and that many more reactions can be carried out in that zone.

One of the other advantages of using a fixed catalyst bed reactor for catalyst testing and/or screening is the fact that the products are continuously separated from the catalyst. This allows an easy evaluation and optimisation of process parameters, without having to change out the catalyst after each change of conditions.

As outlined above, the reactor assemblies for testing and/or screening purposes preferably comprise a flow-through reactor of minimal size; thereto, the reaction chamber is preferably of elongated shape having a diameter of at most 5 cm, preferably at most 2 cm, more preferably at most 1 cm, most preferably having a diameter of 1.7-2.5 mm wherein a chemical reaction in a very small volume with small amounts of reactants and optionally one or more catalysts are possible.

In a preferred embodiment, the dilution fluid(s) supply means discharge in the reactor assembly within at most 10 mm from the downstream end of the reaction zone. In case the reaction zone occupies the reaction chamber in full, the said dilution fluid supply means discharge in the effluent conduit(s) at a distance of at most 10 mm from the reactor outlet. In case the reaction chamber comprises a second space downstream of the reaction zone, the dilution fluid supply means discharge opening is preferably at most 10 mm from the downstream end of the said reaction zone, such as the downstream end of a fixed catalyst bed. Such a distance, in particular when the reaction chamber has the above identified shape and diameter, ensures proper dilution of the reaction mixture, substantially without any hold-up of compounds of the said mixture.

In the reaction zone, gaseous and liquid components can be formed at the reaction conditions used. A gas/liquid mixture often leads to measurement inaccuracies, e.g. by the formation of a slug of gas, followed by a slug of liquid in the effluent stream, resulting in pressure variation in the stream and a non-constant flow thereof, leading to measurement inaccuracies. Further, another problem, caused by the presence of gas in a liquid effluent stream is the fact that liquid analysers, such as GC or HPLC systems cannot properly be used when gas-bubbles are present in the liquid stream. Gas-bubbles will cause a variation of the amount of liquid injected in such systems. Further, the presence of gas in the inlet capillary of a mass spectrograph will cause strong measurements fluctuations and also, spectroscopic techniques, such as Ultraviolet-Visible spectroscopy, Near Infrared spectroscopy or Infrared spectroscopy will strongly suffer from light scattering and liquid displacement because of the presence of gas. Further, for proper testing/screening, the determination of the production rate of gaseous compounds as well as of liquid compounds and quantification thereof is necessary for accurate analyses of the reaction process. It is therefor highly advantageous to separate the liquid and the gaseous components in the effluent stream from each other before being transferred to an analyser. An additional advantage of the invention is the fact that due to the addition of diluent the volume of the effluent stream is considerably increased. This will allow the use of G/L separators with larger internal dimensions without causing unnecessary hold-up of the products. Thus, the effluent conduit preferably comprises a gas/liquid separator, therewith enabling proper separation of the gaseous and liquid components from one another, so that the gaseous phase can be analysed independently from the liquid phase. It is however also possible to discard either one of the said phases and to analyse the not-discarded phase. In some cases it is necessary to add a gas/liquid separator before discharging the effluent to an analyser. This is the case when the reactor effluent consists of a gas and a liquid phase, but also will be necessary when the reactor effluent consists of only liquid and a gas diluent is added, or when the reactor effluent consists of only gas and a liquid diluent is added.

The gas/liquid separator will have at least two outlets, one predominantly containing gas and one predominantly containing liquid, each discharging to a separate analyser. The efficiency of the gas liquid separator is strongly dependent on its size. As the volume of fluid is increased by the addition of diluent, as described in the present invention, it allows the use of a larger gas/liquid separator thus increasing its efficiency.

In order to quantitatively analyse the gaseous or liquid stream, it is of importance that the gas/liquid separator is capable of completely separate the gaseous from the liquid flow. However, such a separation requires high sophisticated gas/liquid separator equipment. In a very attractive embodiment of the present invention, at least two gas/liquid separators are present in the effluent stream, arranged to one another in a serial fashion. In the first upstream separator, a representative amount of either gas or liquid is separated from the remaining effluent stream, that still may comprise a mixture of both gas and liquid. The separated gas or liquid can then be analysed accordingly. In the second, downstream gas/liquid separator, a gaseous flow is separated in case in the first separator liquid was separated or, when in the first separator gas was separated, liquid will be separated in the second gas/liquid separated, possibly leaving a stream still containing gas and liquid effluent leaving the separator. In this way, both gaseous and liquid effluent components can be properly analysed, without the need of sophisticated gas/liquid separation devices. Such devices may in this arrangement be of more simple design, as full separation of gas and liquid is not required. Any not separated gas/liquid mixture can be discarded. Analysis and quantification of the compounds of the effluent stream are preferably performed by incorporation, in the effluent stream, of an internal standard, preferably comprising both a liquid and a gaseous internal standard (see below).

Preferably, the analyser is chosen from the group, consisting of: gas chromatograph (GC), liquid chromatograph (LC), high pressure liquid chromatograph (HPLC), a mass spectrometer (MS), a diffractometer, an Ultraviolet-Visible (UV-VIS) spectrometer, a Infrared (IR) spectrometer, a Near Infrared (NIR) spectrometer, a Nuclear Magnetic Resonance (NMR) spectrometer, a viscosity meter or density meter.

Preferably, the analyser comprises on-line analyser or a sample collection system, or a combination thereof.

Non-limiting examples of on-line analysers are a gas chromatograph (GC), liquid chromatograph (LC), high pressure liquid chromatograph (HPLC), a mass spectrometer (MS), a diffractometer, an Ultraviolet-Visible (UV-VIS) spectrometer, a Infrared (IR) spectrometer, a Near Infrared (NIR) spectrometer, a Nuclear Magnetic Resonance (NMR) spectrometer, a viscosity meter, density meter. These analyzers may be equipped with a sample valve or syringe injection system to allow injection of a small representative sample of the effluent stream.

As mentioned above also a sample collection system can be used for the analysis of samples. In that case the samples are first collected in collection containers before being transferred to one or more analysers. Thus will allow more flexibility of the system, as it is not necessary to integrate the analyser in the whole apparatus. The sample collection system is designed in such a way that it can collect liquid samples in collection containers designed to collect liquids, or it can collect gaseous samples in collection containers designed to collect gas. Examples for liquid collection containers are reactor tubes, vials, wells or the like. Examples for gas collection containers are gas-collection bags (Tedlar bags), gas-tubes, gas pipettes, cold traps, cryogenic traps or the like. The collection containers may be organised in a systematic way, such as for instance in a row, a matrix or a carrousel. Typical examples of such systems are reagent tube racks, 96-well plates, 384-well plate, auto-sampler racks, or carrousel. Most modern analyser systems known in the art are equipped with a so-called auto sampler allowing automatic analysis of a multitude of samples. Preferably the array of collection containers of such collection system is configured in such a way that it is compatible with the auto-samplers of the consecutively used analyser system.

Typically the sample collection system is designed such that at a given time the conduit for the diluted effluent stream is connected to one collection container or to a waste stream. Preferably this connection point is made in such a way that it is disconnectable allowing it to switch between one and another collection container, or to switch from a collection container to a waste stream or visa versa. By having the ability to switch between collection containers one is able to collect more samples of one reactor at different moments in time. This will allow monitoring the catalyst performance as a function of time or monitor its performance under different process conditions. An example of a disconnectable connection point is a tube or needle releasably attached above the array of collection containers allowing drops of liquid to fall in the individual collection containers. When a needle is used, the collection containers can either individually or collectively be sealed with a septum. The presence of such septum will avoid evaporation of the collected liquid and will suppress the negative influence of air. For gas and liquid samples also multi-connection valves may be used to generate such disconnectable connection points. Also sample collection valves may be used, such as made by VICI (Valco Instruments Co. Inc.).

Preferably the collection system should be fully automatic allowing it to change between collection containers, or between a collection container and a waste system in a automatic way. XY, or XY-Z robots or the like are suitable for this and are commercially available as sample collection robots. A typical manufacturer is Gilson Inc.

Additionally if desired, the collection containers may be conditioned by heating or cooling the system. Cooling may prove useful when sensitive samples are collected that deteriorate at room temperature. Heating may prove useful when solidification of crystallisation is to be avoided.

For use in high throughput experimentation where a multitude of reactors is used the sample collection system can either be designed to collect samples in a parallel or sequential way, or in a combination of both. The parallel approach is particular desired, although the sequential way is also useful. In the sequential approach the effluent conduits of the various reactors are connected to a multi-selection valve, having two outlets, viz. a selected steam outlet, and a common outlet. Various examples of such multi-selection valves are made by VICI. This valve will allow selection of one of the streams of the individual reactors to be guided to the sample collection system. The selected reactor effluent is then collected in one collection container. By proper synchronisation between the multi-selection valve and the sample collection system all reactor effluents can sequentially be sampled in the array of collection containers.

In the parallel approach the multitude of effluent conduits of the various reactors are connected to a multitude of connection points. Preferably these connection points are needles or tube outlets assembled in an array. The spacing of the array should be such that the array of needles is compatible with the array of the collection containers. In this way a multitude of reactor effluents can be collected simultaneously in the array of collection containers. It will be clear to those skilled in the art that many different array configurations will be possible. By making the connection points disconnectable it is possible to switch the multitude of outlet of the diluted effluent conduit to more collection containers. This allows collection of effluents at different moments in time for a multitude reactor of effluents. By automating the movement of the array of outlets and the movement of the array of collection containers it will be possible to make the system suitable for unattended operation.

The analyser may thus as well be a sample collector which can be used to collect samples of the effluent stream, which samples can be analysed at another location, if desired.

In a very attractive embodiment, the reactor assembly comprises a plurality of flow-through reactors as defined above. Most preferably, said flow-through reactors are arranged in parallel, therewith enabling the performance of a plurality of parallel testing/screening reactions, wherein the effluent stream (i.e. the reaction products) of each testing/screening reaction can be analysed in parallel or, if desired, sequentially. In this respect, reference is made to the above identified WO 99/64160.

When the reactor assembly comprises a plurality of flow-through reactors, the said assembly preferably comprises a selector valve between effluent conduits of multiple reactors and at least one analyser for selectively connecting one of the said multiple reactors with the said analyser. By such an arrangement, sequential analyses of the reaction products of the different reactions, each carried out in a different reactor, can be analysed by the same analyser.

Such an apparatus is especially suitable for high-throughput experimentation, wherein a large number of testing/screening reactions, using a plurality of reactors, optionally with different reaction conditions, are conducted simultaneously. In an alternative embodiment, it is also possible to connect the dilution fluid supply means directly downstream of the selector valve. Further, when both a selector valve and one or more gas/liquid separators are used in combination, the gas/liquid separator may be placed either upstream or downstream of the selector valve. When placed downstream, a single separator is sufficient for the gas/liquid separation from multiple reactors.

When the reaction in the reaction chamber occurs at elevated pressure, the apparatus may be equipped with one or more back-pressure regulators. Depending on the application and type of such back-pressure regulators, these can be placed at many different positions in the assembly, such as, directly downstream of the reactor outlet, directly downstream of the gas/liquid separator or directly downstream of a multi-selection valve.

Back pressure regulators are used to control the pressure upstream of the regulator and are useful for generating and controlling the pressure in the reactor to a constant value at a wide range of flows. Typical examples of such back pressure regulators are given in WO 01/48575 and EP02075491.7

The skilled person will be able to determine the optimal position and the suitable regulator type to be used in the reactor assembly.

The invention further relates to a process for analysing a fluid effluent stream from a flow-through reactor comprising a reaction chamber having a reaction zone, comprising the steps of:
A) diluting at least 30 w/w % of the effluent stream downstream of the reaction zone with at least one dilution fluid,
B) transferring at least a portion of the diluted effluent stream obtained in step A) to at least one analyser,
C) subjecting the transferred effluent stream to an analysis procedure.

According to this embodiment of the invention, a significant portion of the effluent stream leaving the reaction chamber is diluted, i.e. at least 30 w/w %, preferably at least 50 w/w %, more preferably at least 80 w/w %, even more preferably at least 95 w/w % of the effluent stream is diluted; this is in particular the case when liquid components of the effluent stream are to be analysed. In that case, most preferably the whole liquid phase of the effluent stream is diluted. In case gaseous components of the effluent stream are to be analysed, at least 30 v/v %, preferably at least 50 v/v %, more preferably at least 80 v/v %, even more preferably at least 95 v/v % of the effluent stream is diluted; most preferably the whole gaseous effluent stream is diluted in that case. This is in contrast to sampling methods, known in the art, wherein only an insignificant small amount, i.e. less than 5 w/w % or 5 v/v %, of a reaction mixture is withdrawn from the reactor and diluted for analysis. In this respect, reference is made to U.S. Pat. No. 6,178,830.

Such a process is in particular advantageous, when the reaction taking place in the flow-through reactor is performed for analyses purposes, e.g. to establish optimal reaction conditions and for testing/screening purposes. As such reactors are preferably designed to be as small as possible, the effluent stream is usually as low as 1 ml/min or less, preferably 0.5 ml/min or less. As it has been proven to be very difficult to analyse such effluent streams with accuracy, in particular when the said stream comprises both gaseous and liquid components or other immiscible components, it is been found that diluting the whole effluent stream downstream of the reaction zone with a dilution fluid results in a stream of larger volume that can be analysed with high accuracy. The said diluted effluent stream, or at least a portion thereof, is transferred to at least one analyser, e.g. through a effluent conduit as indicated above. It will be clear to the person skilled in the art, that not the whole diluted effluent stream has to be transferred to an analyser, but that a portion thereof may be sufficient. Since most analytical equipment has a high sensitivity and reproducibility, it is possible to obtain very reproducible and accurate analysis results, even at relatively high levels of dilution. Examples of analysis procedures are indicated above.

It is to be noted that the diluted effluent stream can be splitted in multiple streams, that can be transferred to different analysers to be subjected to multiple analyses procedures.

As mentioned above, with the process according to the present invention it is e.g. possible to detect the mass flow rate of each individual component in the liquid mixture and/or gas phase. This can be accomplished by accurately recording the amount of diluent(s) added per unit of time. Now based on the concentration of the liquid components in the diluted solution the production rate can be determined by:

$$M_x = C_x \cdot M_{solvent}$$

Where $M_x$ is the molar flow of component X (mmole/minutes) exiting the reactor, $C_x$ is the measured ratio between the concentration of component X in the solution (mmole/ml) and the concentration of the solvent (mmole/ml). $M_{solvent}$ is the molar flow of the solvent leading into the apparatus. To facilitate the calculation of $M_x$ internal standard may be added to the solvent with a pre-set concentration. The exact determination of the concentration depends on that type of analyser used and is known to those skilled in the art.

In an attractive embodiment, the effluent stream is diluted in the reaction chamber, downstream of the reaction zone. As indicated above, the whole effluent stream can conveniently be diluted by introducing a single dilution fluid stream into the reaction chamber. However, it is also possible for the dilution fluid to be introduced into a conduit, transferring the effluent stream from the reaction chamber to e.g. an analyser. However, in case multiple conduits are connected to the reaction chamber, the dilution fluid should preferably be introduced before the branching into the said multiple conduits, or be introduced into each of such conduits in order to dilute the whole effluent stream.

Advantageously, a pre-selected amount of dilution fluid is supplied to the effluent stream.

With a "pre-selected amount of dilution liquid" is meant such an amount that is suitable to dilute the effluent stream to such an extent that a sufficient amount of effluent stream is collected from the reactor allowing an accurate analysis to be performed. Usually, substantially the whole effluent stream will be collected. The pre-selected amount may be in the form of a single pulse of dilution liquid, a discontinuous series of pulses, but will preferably be in the form of a controlled and/or pre-determined continuous flow. Herewith measurements on concentrations, fluxes and production rates can accurately be performed.

Preferably, a dilution fluid, in particular a liquid, is used provided that the said fluid has no adverse effect on the effluent stream. However, a gaseous dilution fluid, or a combination of liquid and gaseous diluent fluids can be used, optionally provided via separate dilution fluid supply means. Preferably, the dilution fluid comprises a preferably inert liquid wherein the effluent stream is dissolved or at least dispersed to generate a free flowing solution of at least the liquid components of the effluent stream. For the analyses of e.g. non-polar organic compounds, the dilution fluid may e.g. comprise heptane, toluene or butyl acetate, whereas for highly polar organic compounds, e.g. methanol, acetic acid or water can be used. When a gaseous dilution fluid is used it preferably has no adverse effects on the effluent stream and/or on the analyser. Preferably it should be chemically inert and cheap. Preferably it also should not be the same gas as used in the reaction mixture, allowing the estimation of the dilution ratio by analysis of the gas composition of the diluted effluent.

The skilled person is however able to determine the proper (liquid and/or gaseous) dilution fluid to be used for the envisaged aim. As outlined above, the diluent fluid may also comprise a gas; the advantages of using a gaseous dilution fluid are, among others:

a) By the addition of diluent gas, gaseous components exiting the reaction zone will be swept to the analyser, making the residence time in the downstream piping significantly shorter. In this context the diluent will act as a purge gas.

b) By dilution by the purge gas the partial pressure of components will be lowered. For components with a high vapour pressure this allows keeping these components in the gas phase, and avoid condensation. The lower partial pressure will also lower the tendency to adsorb on the surface also leading to long residence times.

c) By dilution by the purge gas and the resulting lower partial pressure of the components exiting the reactor zone will lower the chance of undesired consecutive reactions in the downstream piping. For instance it is well known that reactive components such as dienes or epoxides may react without the presence of a catalyst.

d) When the flow rate of the dilution gas is monitored, it is possible to calculate the production rate of the individual gaseous components based on the concentration of the dilution gas and the concentration of the individual gaseous component in the effluent gas. This is even further facilitated by the addition of an internal standard to the diluent at a known concentration.

e) In case of a gas/liquid system exiting the reactor, the addition of extra purge gas will facilitate the downstream gas/liquid separation, especially when also liquid diluent is added.

The advantages of a liquid diluent fluid are, among others:

a) Due to the addition of dilution liquid, liquid components exiting the reaction zone will be swept to the analyser, making the residence time in the downstream piping as short as possible. The diluent will act as a purge liquid.

b) Due to the dilution by the purge liquid the concentration of components with a high tendency to crystallise will be lowered thus causing these components to stay in the liquid phase. The lower concentration in the liquid phase of such components will also lower the tendency to selectively adsorb to the surface.

c) The addition of dilution liquid will decrease the viscosity of the liquid exiting the reactor zone.

d) In some particular cases the addition of dilution liquid will allow extraction/scrubbing of gaseous components allowing a simplified analysis of all component of the effluent stream.

e) The dilution with the dilution liquid and the resulting lower concentration of the dissolved components exiting the reactor zone will lower the chance of undesired consecutive reactions in the downstream piping. For instance it is well known that reactive components such as dienes or epoxides may react even without the presence of a catalyst. In addition it is possible to add quenching components (see also conditioning components) in the diluent to avoid any consecutive reaction of intermediates.

f) When the flow rate of the dilution liquid is monitored, it is possible to calculate the production rate of the individual gaseous components based on the concentration of the dilution gas and the concentration of the individual gaseous component in the effluent liquid. This is even further facilitated by the addition of an internal standard to the diluent at a known concentration (see below).

g) In case of a gas/liquid system exiting the reactor, the addition of extra diluent liquid will facilitate the downstream gas/liquid separation significantly.

h) It is easy to add an extra conditioning component to the purging liquid. This conditioning component will react with the reaction products, thus changing its chemical and physical properties. This will improve the stability of these components, and/or facilitate their sequential analysis.

As indicated above, the method according to the present invention is particularly suitable for small scale reactors for performing analytical, testing and screening reactions, wherein the effluent stream, when leaving the reaction zone has a liquid flow rate of below 1 ml/min, in particular below 0.5 ml/min, and/or a gas flow rate of less than 100 Nml /min, in particular less than 50 Nml/min.

For the case where the effluent stream is diluted with a liquid diluent, the ratio in the diluted effluent stream, between volumetric diluent liquid flow: volumetric reactor liquid effluent flow is preferably 0,2-10,000:1, more preferably 1-1,000:1 and most preferably 10-100:1.

For the case where the effluent stream is diluted with a gaseous diluent, the ratio, in the diluted effluent stream, between volumetric diluent gas flow; volumetric reactor gas effluent flow is preferably between 0,1 and 1000, more preferably 0,1-1,000:1, more preferably 0,5-100:1, most preferably 10-1:1. By increasing the ratio, the sampling speed is increased.

In both gas and liquid cases with too low dilution ratios no substantial advantages of the diluent can be obtained. On the other hand a too high dilution ratio may result in unnecessary high diluent consumption and a too dilute stream to allow proper and accurate analysis in the analyser.

The optimal ratio between the diluent and the effluent stream depends on several factors and will therefore vary depending on the type of application. The upper limit of this ratio is often defined by the sensitivity of the analytical equipment or may be limited by e.g. the vial size of an auto collector robot. The lower limit is mainly defined by the solubility of the liquid components of the reactor effluent and by the rate, desired to transport the effluent liquid from the reactor to the analyser.

In a very attractive embodiment of the process according to the invention, the diluted effluent stream is subjected to a gas/liquid separation step before being subjected to the analysing procedure, providing a gaseous and a liquid effluent stream. Such a separation step can be performed using one or more gas/liquid separations, as described above. This embodiment is in particular relevant when the effluent stream, leaving the reaction zone comprises a liquid and a gaseous component, or when a gaseous diluent is added to a liquid effluent stream or a liquid diluent is added to a gaseous effluent stream. The presence of liquid and gaseous components causes several problems in the analyses procedures. For example, a slug of gas reactant, followed by a slug of liquid in the conduits wherein the effluent stream is transferred to e.g. an analyser, may cause pressure variation in the effluent stream, resulting in a non-constant flow and to measurement inaccuracies. Further, the presence of gas and liquid may cause problems with respect to pressure control by a downstream pressure regulator.

One of the most obvious problems caused by the presence of gas in the liquid is the fact that most liquid analysers can not cope with gas bubbles in the liquid stream. For GC or HPLC systems gas bubbles will cause a variation of the amount of liquid injected when using injection valves. In the inlet capillary of a MS it will cause strong fluctuations and spectroscopic techniques such as UV-VIS, NIR or IR will strongly suffer from the light scattering and liquid displacement when gas bubbles are present in the measuring cuvette, and even when trying to collect the liquid with a auto-collector robot the presence of gas may lead to uncontrolled flow of liquid into the collection vials.

Another problem is the fact that very often one would like also to be able to measure the gas composition of the gas portion of the effluent stream. Although most of the above mentioned techniques can also be set-up to analyse gaseous samples, no analysers are known to exist that measure both components within one instrument. To enable separate analysis of gas and liquid on at least two separate analysers both phases need to be separated first.

In addition, most gas analysers have large difficulties to cope with liquid droplets. In a GC it may ruin the column or injection valve, in a MS liquid may plug the inlet capillary and in spectroscopic techniques it will interfere with the light beam and contaminate the cuvette.

Another problem when dealing with reactor effluents consisting of a gas/liquid mixture is the fact that one also would be interested in measuring the production rate (mass flow) of both phases to be able to perform a proper mass balance over the reactor. The gas-liquid separation step can be performed by gas/liquid separator devices that are known in the art. By the addition of diluent(s) to the effluent stream the gas/liquid separation is highly facilitated. This is caused by the fact that the gas/liquid separator now can be designed for larger volumes allowing it to have a better separation and a lower relative fluid hold-up.

Preferably, both the gaseous and liquid effluent streams from an effluent stream are separately subjected to an analysing procedure, enabling determination of both the gaseous and liquid components of the effluent stream. However, if only the gaseous or the liquid components of the effluent stream are to be analysed, the other stream may be discarded.

Preferably, the dilution fluid is supplied as a constant flow. Herewith, a fixed amount of dilution fluid is supplied. Thus, production rates can be easily calculated from the concentrations of certain components in the effluent stream based on mass balance, in particular when an internal standard is incorporated (see below).

To obtain a proper mixture of the effluent stream and the dilution fluid, the said effluent stream and dilution fluid may be properly mixed at the location wherein the stream and the fluid are combined.

An internal standard is particularly useful when the analyser is not able to detect the concentration of the diluent in the diluted effluent. This may be the case when the concentration of the diluent is too high causing the analyser to run out of scale, or it may be that the diluent cannot be detected by the analyser. The concentration of the internal standard can be chosen such that is in the same order of magnitude as the concentration of the diluted reaction products in the diluted effluent.

When the internal standard is added to a liquid reaction mixture or diluent, the internal standard used is preferably soluble in the said reaction mixture or diluent liquid at its used concentration and it should be easily detectable by the analyser when present in the diluted effluent stream mixture. Preferably it should have a low vapour pressure to avoid evaporation of the internal standard, and it should be inert to the components of the reactor zone effluent. Those who are skilled in the art will recognise that the proper choice of such internal standard will largely depend on the application and on the analyser used. Some examples for useful liquid internal standards are e.g. octane, xylene and dibutylether.

The internal standard is preferably added before step c). Said internal standard can be added to the reaction zone, e.g. together with the reactants and/or being incorporated in the dilution fluid. However, other ways of adding the internal standard are also possible, such as by separately adding thereof in the effluent conduct(s). Also multiple internal standards can be added, e.g. a combination of a liquid and a gaseous standard, that may be added together or separately.

In some special cases one may additionally add one or more conditioning compound(s) to the diluent fluid. This conditioning compound will react with one or more of the components of the reactor effluent, resulting in derivative components with a different chemical property such as for instance a lower reactivity, higher stability or lower corrosiveness. Such method may also be used to generate components with different physical properties, such as lower viscosity, higher boiling point, lower boiling point, higher melting point or higher solubility. Such change of property may facilitate the downstream handling of the components. Alike methods are well known in analytical chemistry and known under the name of derivatizing agents. A typical example of such conditioning compound is diazomethane that may react with non-volatile organic acids to produce the far more volatile, more soluble and less corrosive methyl ester. Such conditioning compound should be present at a concentration high enough to convert all the components in the reactor effluent to their corresponding conditioned derivative. Those who are skilled in the art will recognize that the choice of the conditioning compound is strongly dependant of the application and the analytical method. It will be clear that many different methods and compounds can be used.

Also to gas diluent an internal standard can be added, with almost the same functionality, use and constraints as with the liquid internal standard. In contrast with the liquid internal standard preferably it should have a high vapour pressure to avoid condensation of the internal standard. Also it should not dissolve significantly in the liquid diluent. Those who are skilled in the art will recognise that the proper choice of such internal standard will largely depend on the application and on the analyser used. Examples for useful internal standards are e.g. krypton, xenon, helium, carbon dioxide or methane.

The invention also relates to a process as described above, for analysing the fluid effluent streams for a plurality of flow-through reactors, each reactor comprising a reactor chamber having a reaction zone, comprising the steps of:

A) diluting at least 30 w/w % or at least 30 v/v % effluent stream of each reactor downstream of the reaction zone with a dilution fluid, B) selectively transferring at least a portion of a first effluent stream from a first reactor obtained in step A) to at least one analyser, C) subjecting the first transferred effluent stream to an analysis procedure, D) selectively transferring at least a portion of a second effluent stream of a second reactor obtained in step A) to at least one analyser, E) subjecting the second transferred effluent stream to an analysis procedure, and, optionally, F) repeating steps D) and E) for any effluent stream of a following reactor.

Such a process is particularly advantageous when multiple reactions are carried out in parallel to test/screen for e.g. optimal reaction conditions. However, the above described sequential sampling method can also be used in this process, although, for sampling procedures, parallel sampling as described above is preferred. When the reaction products, produced in the reaction zone of the reaction chamber are leaving the said reaction zone as effluent stream, the said significant portion of the effluent stream of each reactor is diluted. At least a portion of such a diluted effluent stream from one of the said reactors is transferred to at least one analyser or optionally to a plurality of analysers, wherein is also possible that a portion of the said diluted effluent stream is discarded. In order to avoid the necessity to have a separate analyser for each reactor, the effluent streams from the multiple reactors are selectively transferred to the analyser(s). This means that the effluent stream from a first reactor is transferred to one or more analysers, whereas the effluent stream of other reactors are refrained from being transferred or e.g. being stored in a buffer compartment for later analyses. As the transferred effluent stream has been subjected to the analyses procedure in the analyser, the analyser will be ready for a next analyses procedure of a following effluent stream. Then, at least a portion of a second effluent stream from a second reactor can be transferred to the said analyser to be subjected to the analyses procedure. These steps can be repeated until the desired number of effluent streams have been subjected to the envisaged analyses procedures. The plurality of flow-through reactors can be arranged in a parallel manner, e.g. according to the teaching of WO 99/64160.

DETAILED DESCRIPTION OF THE INVENTION

Figure 1A:
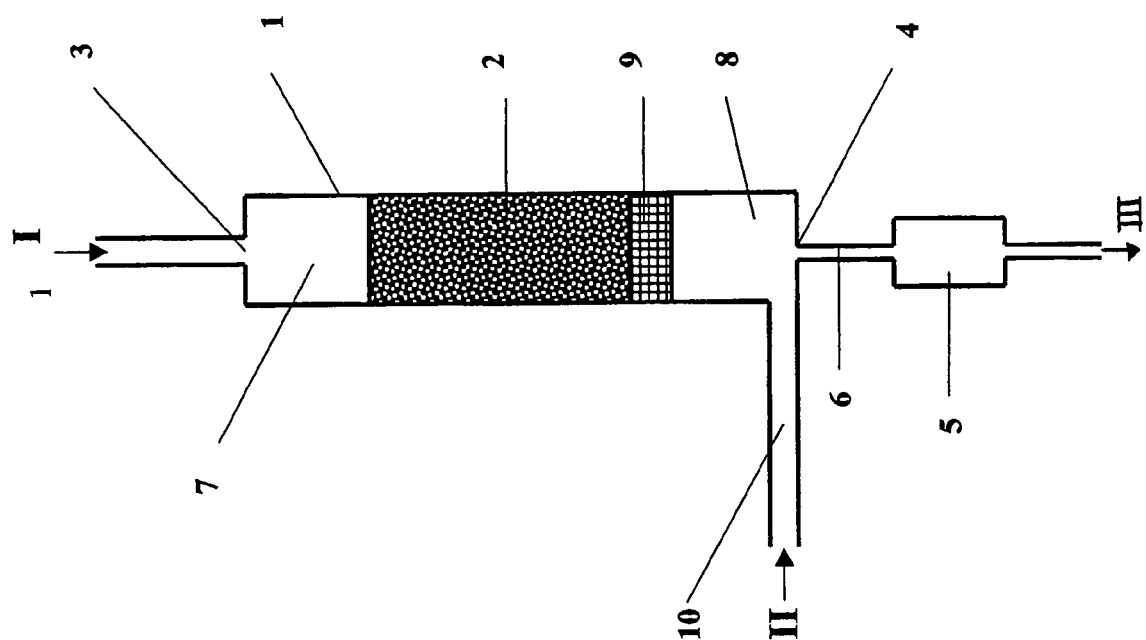
FIGS 1a-f show schematical cross sections of reactor assemblies according to the present invention.

In FIG. 1a, a reactor assembly is shown, comprising a flow-through reactor, comprising a reaction chamber 1, accommodating a reaction zone 2, such as a catalytic fixed bed and an inlet 3 for inflow of at least one of the reactants. The direction of the inflow is shown with arrow I. The reactor further comprises a first space 7, upstream of the reaction zone and a second space 8, downstream of the reaction zone. The downstream end of the reaction zone is in this case formed by a grid 9, holding the fixed catalytic bed in place. The reactor further comprises an outlet 4 for an effluent stream from the reactor, the direction of the effluent stream being indicated with arrow III. The outlet 4 is connected to an analyser 5 by an effluent conduit 6. Although a single outlet and a single effluent conduit is shown, the second space 8 may comprise multiple outlets, each being connected to an effluent conduit and wherein each effluent conduit may be connected to an analyser. Further, dilution fluid supply means designed as a tubing 10 discharge in the reaction chamber, downstream of the reaction zone, in the second space 8. The direction of the flow of dilution fluid is indicated by arrow II.

Figure 1B:
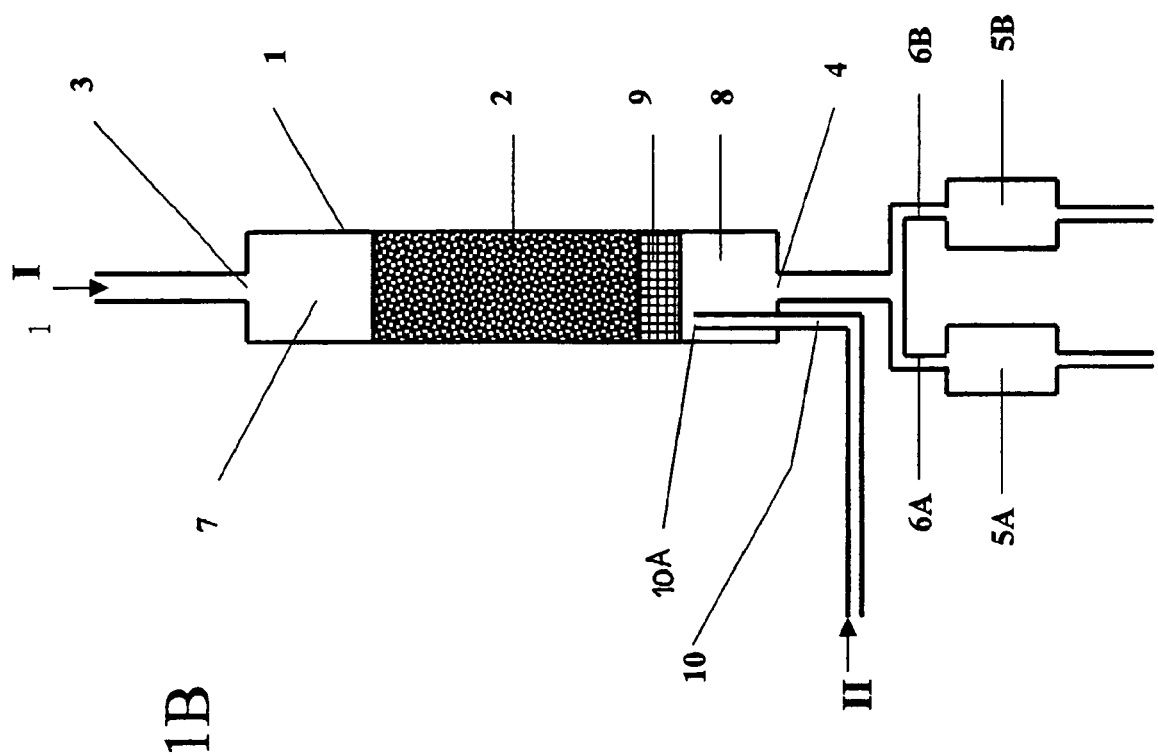
Figure 1C:
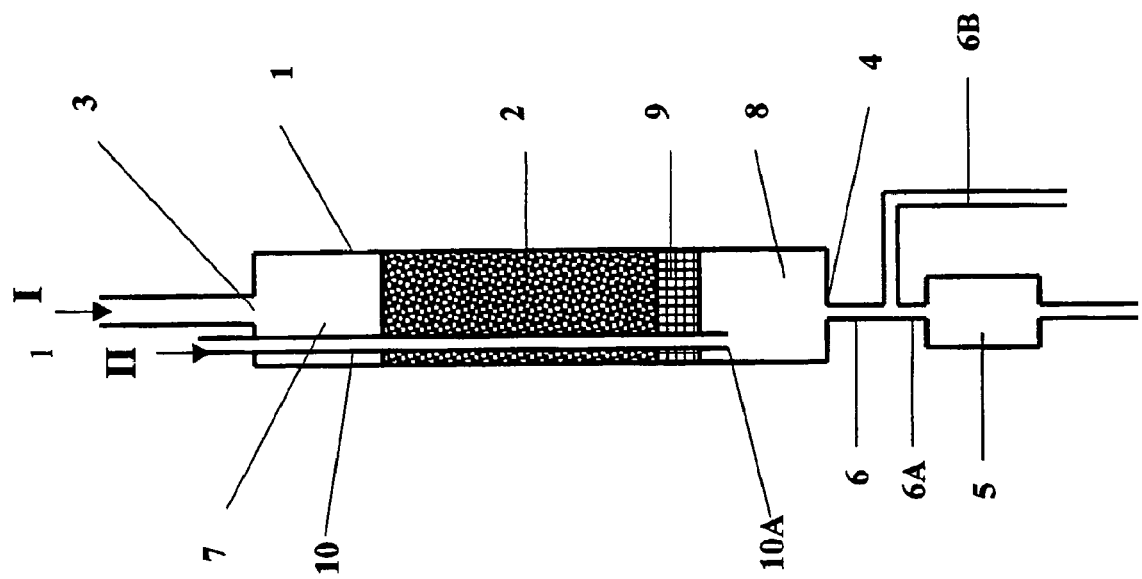
Figure 1D:
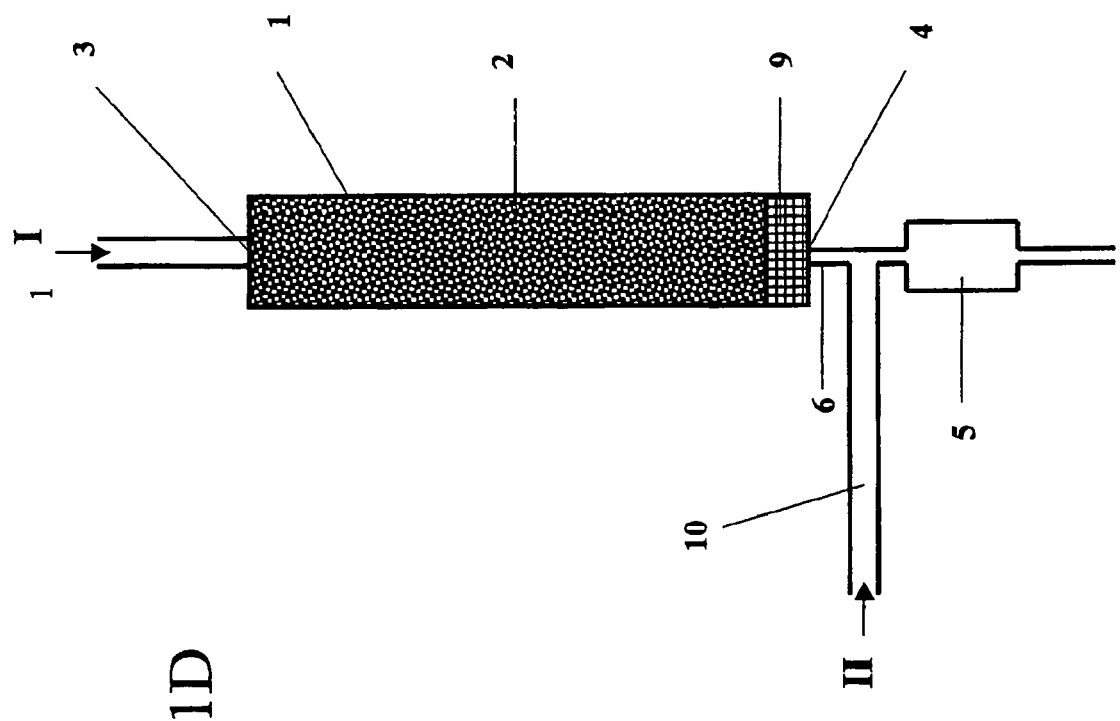
Figure 1:
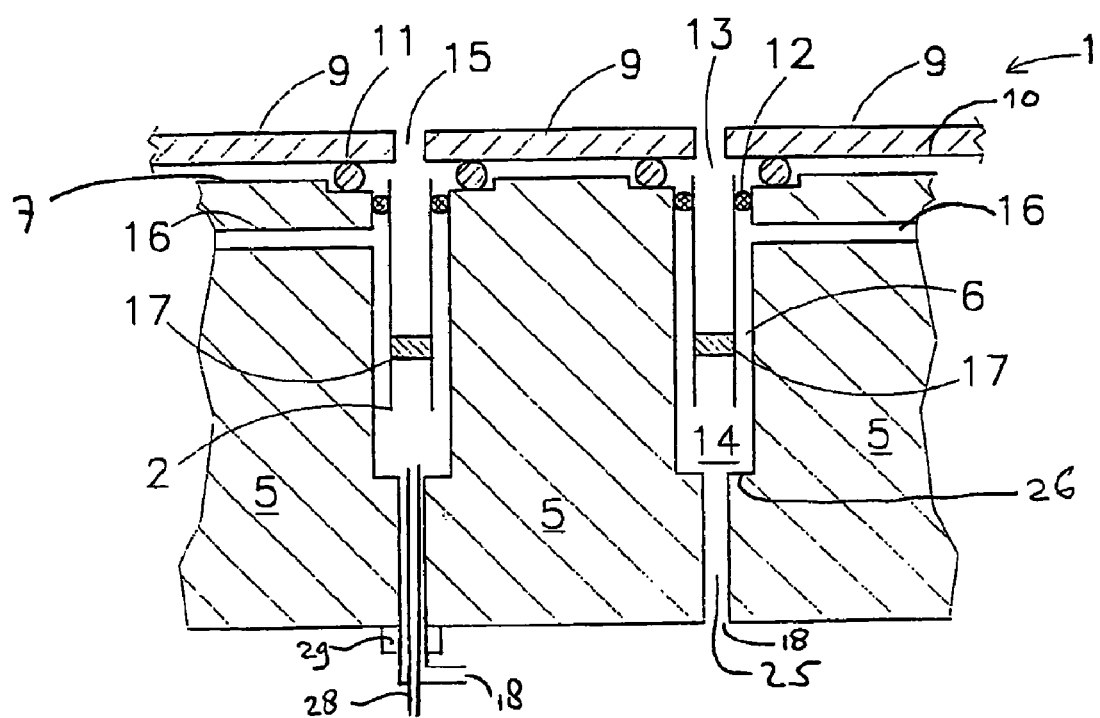

In FIG. 1b, a similar reactor assembly is shown, wherein the reference numbers of FIG. 1 are used for similar or analogous features. The dilution fluid supply means have a discharge opening 10, directing a stream of dilution fluid towards to the bottom of the reactor bed. I.e. the downstream end of the reaction zone. The effluent conduit 6 branches in conduits 6a en 6b, each of the said conduits being connected to an analyser, 5a and 5b respectively.

In FIG. 1c, the dilution fluid supply means enter the reaction chamber at the upstream side thereof, and being directed parallel to the direction of the inflow I. The dilution fluid supply means 7 comprise an elongated tubing 11 entering the reaction chamber at the upstream side thereof, said tubing extending through the first space 7 and reaction zone 2, having a discharge opening 10a in the second space, close to the downstream end of the reaction zone 2. Effluent conduit 6 branches in conduit branch 6a and 6b respectively, conduit branch 6a being connected to an analyser 5. Conduit branch 6b may e.g. be connected to a waist outlet or a buffer vessel.

In FIG. 1d, the reaction chamber 1 comprises reaction zone 2, substantially fully occupying the reaction chamber. The single reactor outlet 4 is connected to analyser 5 by effluent conduit 6. In this case, the dilution fluid supply means 10 are connected to the effluent conduit 6.

In FIG. 1e a schematic cross-sectional view of an reactor arrangement according to the present invention is shown in partly assembled state. The system comprises a housing 1 for housing a plurality of essentially tubular reaction chambers 2 having an inlet 13 and an outlet 18 at the opposite ends thereof. The reactors 2 may be embodied as tubes of metal or other suitable material.

The housing 1 comprises a base block 5 and a cover element 9. The base block 5 has a plurality of through going first channels 6 formed therein for removably housing the reactors 2. The cover element 9 is provided here with third channels 15 each connecting to an inlet 13 of the reactor 2.

The first channels 6 are formed here as bores in the solid base block 5. However other designs, wherein a first channel 6 is entirely or partly formed by a tubular part of the base block 5 are also possible.

The reactors 2 have a length such that each reactor 2 is entirely accommodated within the first channel 6.

It can be seen that an extension channel 25 is formed extending coaxial and in line with the first channel 6. The extension channel 25 extends between the lower end of the first channel and the second face 8 of the base block 5. The extension channel 25 has a smaller diameter than the first channel 6, so that an annular shoulder 26 is formed.

The reactor 2 can be designed to rest upon this annular shoulder 26.

A first face 7 of the base block 5 is facing towards the cover element 9. The cover element 9 is releasable attachable on the first face 7 of the base block 5. There may be fastening means provided, such as screws, to attach the cover element 9 to the base block 5.

Between the first face 7 of the base block 5 and the bottom surface 10 of the cover element 9, a number of high pressure resistant O-rings 11 are provided as first sealing elements. These O-rings 11 are placed such that the O-ring 11 is near the inlet 13 of the first channel 6 and surrounds this inlet 13. Hereby leakage between neighbouring first channels 6 is prevented.

As is shown, annular grooves are provided in the first face 7 of block 5 for receiving the O-ring 11. This also prevents movement of the O-rings 11 in case of a horizontal movement of the cover element 9. Alternatively, the annular grooves may be provided in the bottom surface 10 of the cover element 9.

The housing 1 is further provided with resilient O-rings 12 acting as second sealing elements. These O-rings 12 are located in the first channels 6 of the base block 5.

The reactors 2 each contain a reaction zone 17, for example containing a catalyst in the form of a catalyst bed.

The base block 5 comprises fourth channels 16 opening into zone 14, i.e. the space in first channel 6 outside the reactor 2 and below the second sealing element 12, downstream of the reaction zone 17.

The fourth channels 16 can be used for example for purging or diluting purposes. For example the fourth channel 16 may be in fluid communication with a pressurised source of an inert fluid such as $N_2$, or may be any other dilution fluid, that also may comprise a liquid.

To prevent condensing of the product obtained in the reactor zone 17, if a gaseous product is obtained, an inert gas such as $N_2$ can be fed by fourth channel 16 to force the product obtained in the experiment through the outlet 18 of first channel 6. Herewith a very easy diluting of the product gas can be obtained and condensing can be prevented.

In a possible application of the system of FIG. 1e, a fluid to be treated is fed via third channel 15 to the inlet 3 of the vessel 2. This third channel 15 will of course usually be provided with further sealing means or valves to prevent the fed fluid from returning to the third channel 15. After passing the reactor zone 17 the treated fluid will enter the zone 14 and be discharged via outlet 18.

In practice second channels 16 are preferably used for feeding dilution fluid, such as a gaseous dilution fluid whereas third channels 15 are preferably used for feeding reactants to the reaction, such as liquid, but possibly also gaseous reactants. For the feeding of a liquid for instance, a capillary may be used, which may be partially inserted in the third channel 15. In this arrangement any dilution fluid passing through channel 16 is subjected to temperature conditioning as the reactants in the reaction zone.

The assembly furthermore shows the possibility to arrange a dilution fluid conduit 28 such that it extends into the extension channel 25. A fourth sealing means 29 is provided in this example to seal the annular gap between the second fluid conduit 28 and the base block 5.

The second fluid conduit 28 could be designed as a capillary, e.g. for feeding a liquid dilution fluid into the space below the vessel 2, i.e. without entering the temperature conditioned reaction zone. The diluted effluent stream can be removed via the extension channel 25. When a conduit 28 is present, conduit 16 an be absent or be used for other purposes, e.g. for adding conditioning fluid, without diluent fluid.

Figure 1F:
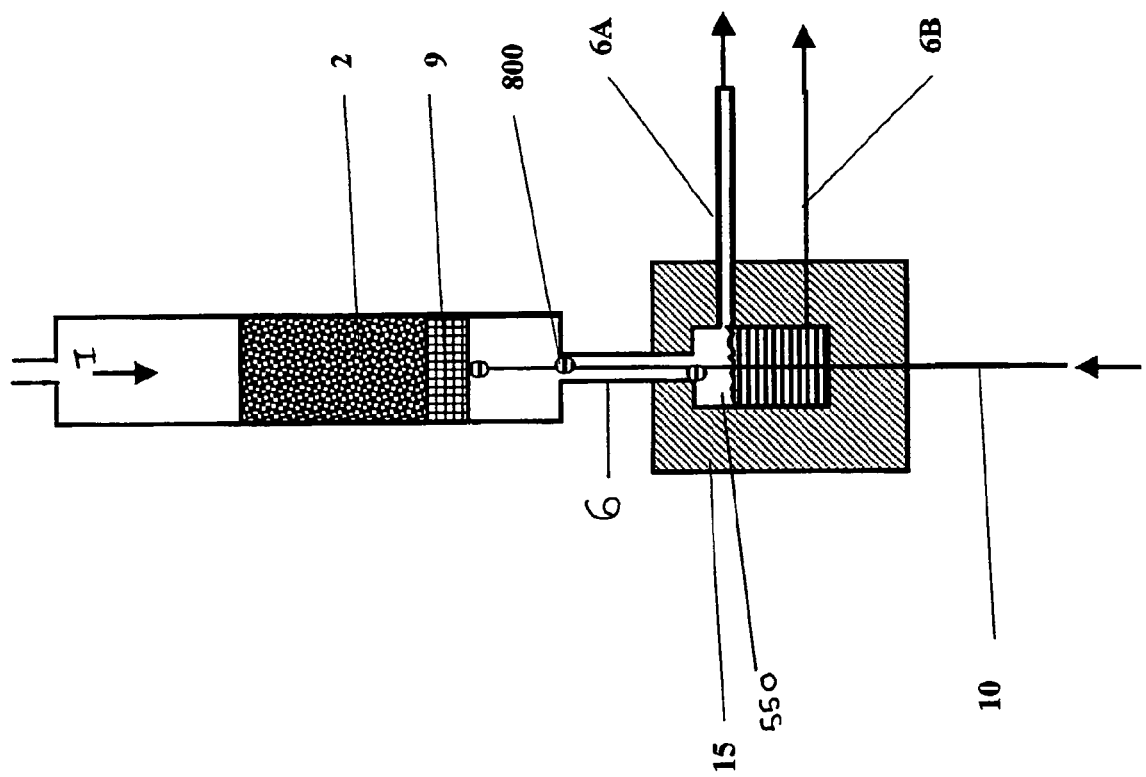

In the arrangement according to FIG. 1f, a liquid dilution fluid supply means 10 enters the reactor 1, the diluent fluent supply means having a discharge opening, close to grid 9 and directing a stream of dilution liquid towards the said grid. Effluent conduit 6 enters a gas/liquid separator 15, comprising a chamber 550 having an outlet 6b for transporting a representative portion of the liquid effluent to an analyser (not shown). Outlet 6a transports all the gaseous effluent and any remainder of liquid effluent. Chamber 550 may be equipped with mixing elements (not shown). The liquid diluent, discharged from the liquid diluent supply means 10, contacts grid 9, therewith mixing with the liquid components of the effluent stream, leaving the reaction zone 2. The mixture of liquid dilution fluid and the liquid components of the effluent stream (droplets 800) are collected in chamber 550 of the gas/liquid separator 15. A representative portion of the liquid components of the effluent stream, mixed with the liquid diluent fluid, leaves the gas/liquid separator 15 via outlet 6b, whereas the gaseous components and any remainder of liquid effluent leave the gas/liquid separator 15 via outlet 6a. In this arrangement, chamber 550 also acts as mixing and buffer chamber.

It is to be understood that the arrangements of the effluent conduits and reaction chambers of FIGS. 1a-f can be interchanged among one another. It is however to be understood that the arrangement of the dilution fluid supply means (10 in FIGS. 1a-d and f, and 26 and/or 28 in FIG. 1e) may discharge both in the second space and/or in the effluent conduits when a second space is present in the reaction chamber. When the reaction chamber does however not comprise such a second space, e.g. as in FIG. 1d, it is preferred to have the dilution fluid supply means connected to the effluent conduit, which will be illustrated in the following drawings.

It is to be understood that in the conduits, means for controlling the flow can be present, such as pressure regulators, flow restrictors, filters or check valves. Typical examples for a flow restrictor are needle valves, capillaries, filters or orifices.

Further, a gas/liquid separator can be present in the effluent conduits. Also means for buffering and additional mixing can be present. A typical buffering and mixing system is a vessel or other system with a low length to diameter ratio. Also static mixers can be used.

Figure 2:
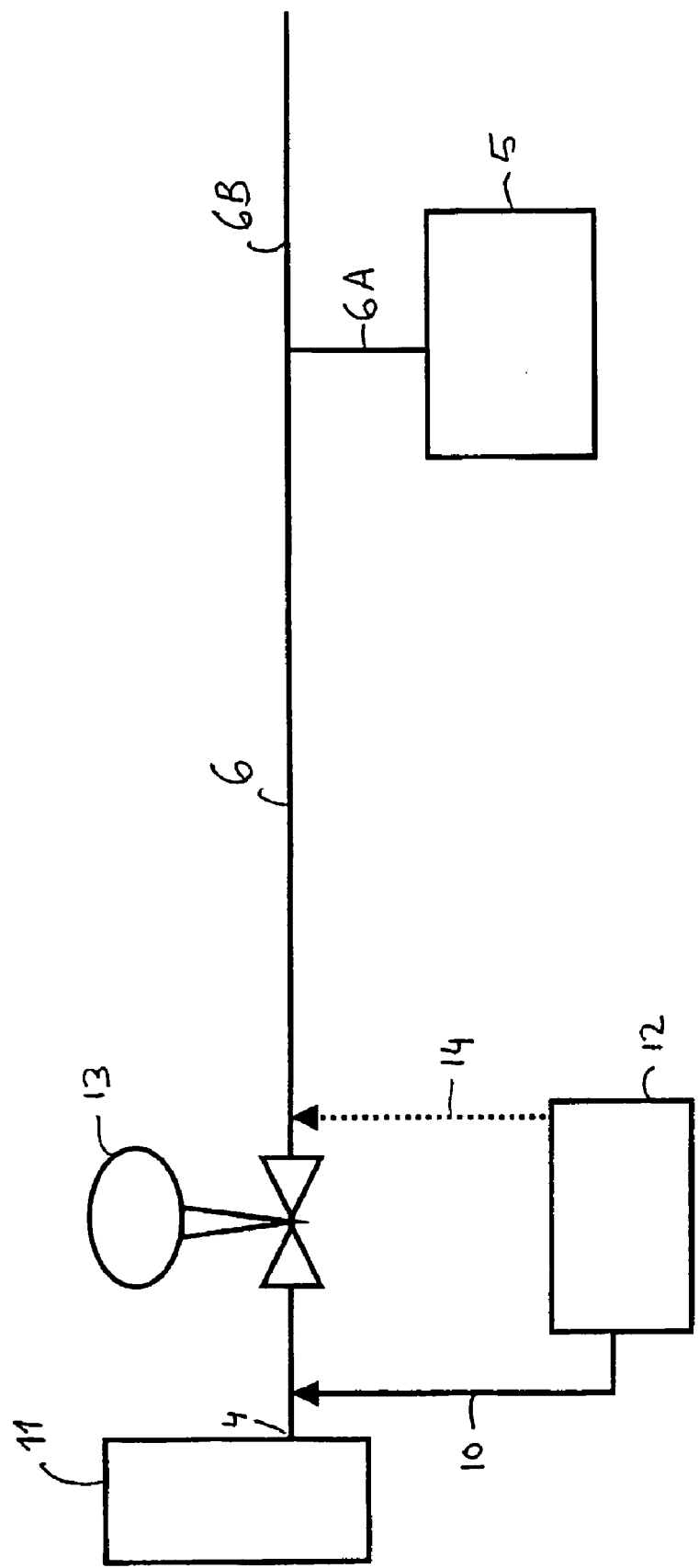
FIGS. 2-5 are schematical diagrams of different embodiments of the reactor assembly according to the present invention.

In FIG. 2, a simple arrangement of the assembly according to the invention is schematically shown. Reactor 11 comprises a reactor outlet 4, being connected to an effluent conduit 6, which is connected to effluent conduit 10. The dilution fluid is stored in container 12. Effluent conduit 6 comprises a pressure regulator 13, and branches into conduit branch 6a and 6b. Conduit branch 6a is connected to an analyser 5. Conduit branch 6b can be connected to another analyser or can be used as waste outlet (not shown). The dotted arrow 14 indicates an alternative connection of the dilution fluid supply means to effluent conduit 6 downstream of the pressure regulator In most cases addition of diluent fluid upstream of the pressure regulator is preferred, as it will facilitate the function of the pressure regulator. However, in some cases addition downstream of the pressure regulator is preferred, for instance when one is not capable in pressurising the dilution fluid. One may also decide to have one diluent upstream of the pressure regulator and one other diluent fluid downstream of the pressure regulator.

Figure 3:
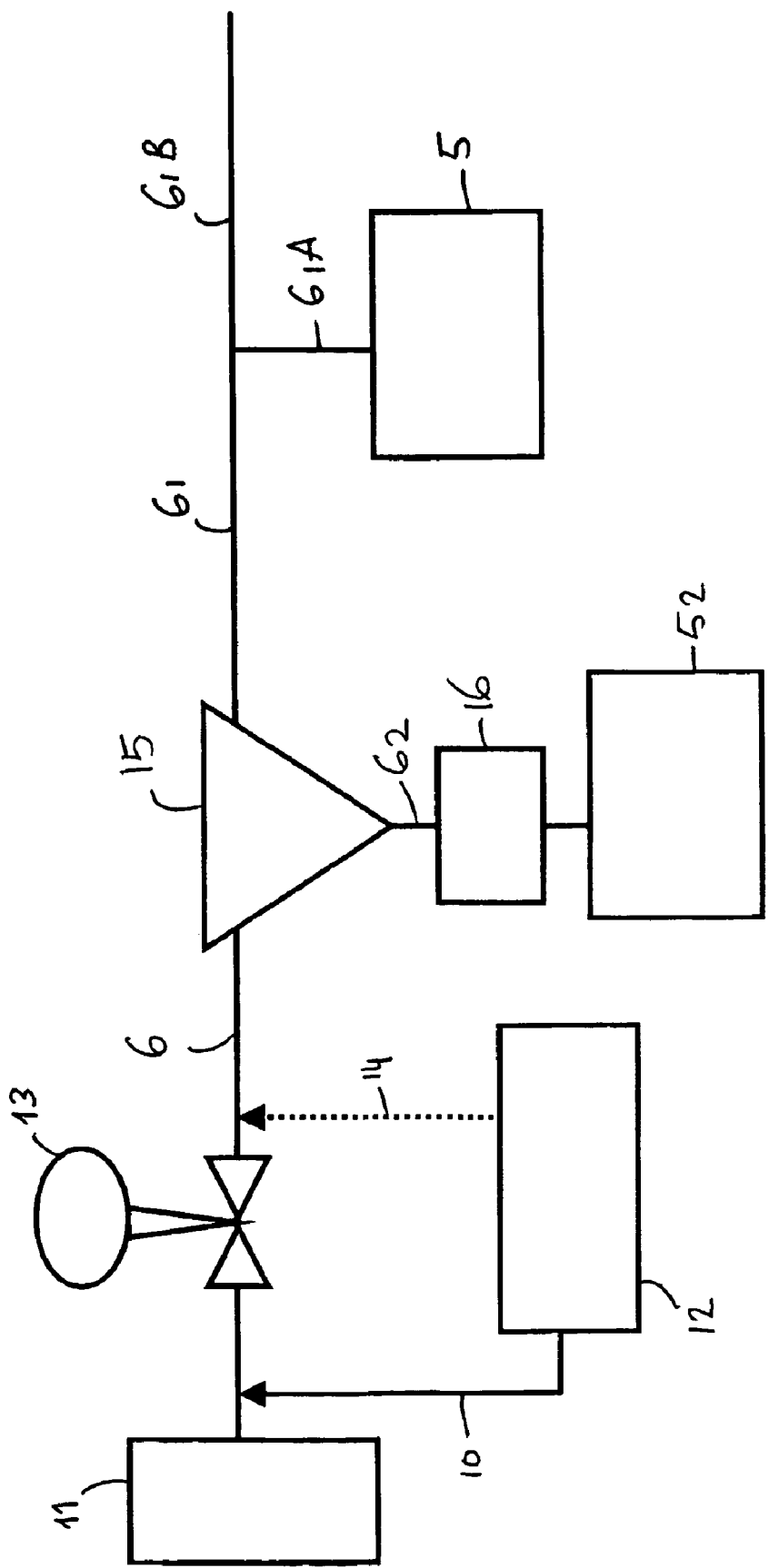
Figure 4:
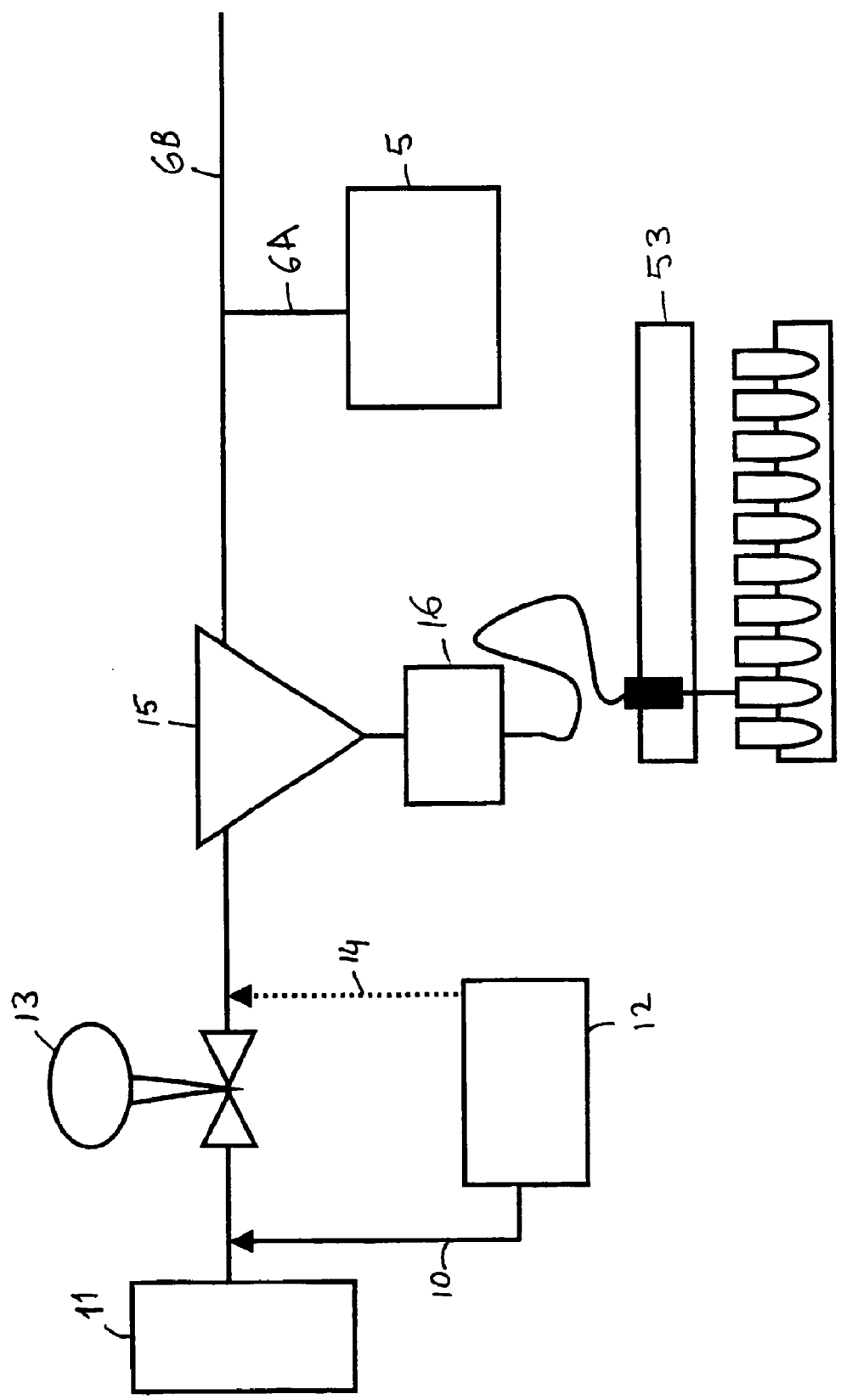

In FIG. 3, the same reference numbers are used as in FIG. 2 for similar or analogous features; in this case, a gas/liquid separator 15 is present in conduit 6, separating the gaseous components of the effluent stream, transferred to the effluent conduit 6 into effluent conduit 61 for gaseous components and effluent conduit 62 for liquid components. Effluent conduit 62 is connected to a liquid analyser 52; in the effluent conduit 62, a pump 16 is present. Conduit 61 branches into conduit 61a, being connected to gas analyser 5, and into conduit 61b. In FIG. 4, a similar assembly as in FIG. 3 is shown, wherein the liquid analyser is a sample collection robot 53.

Figure 5:
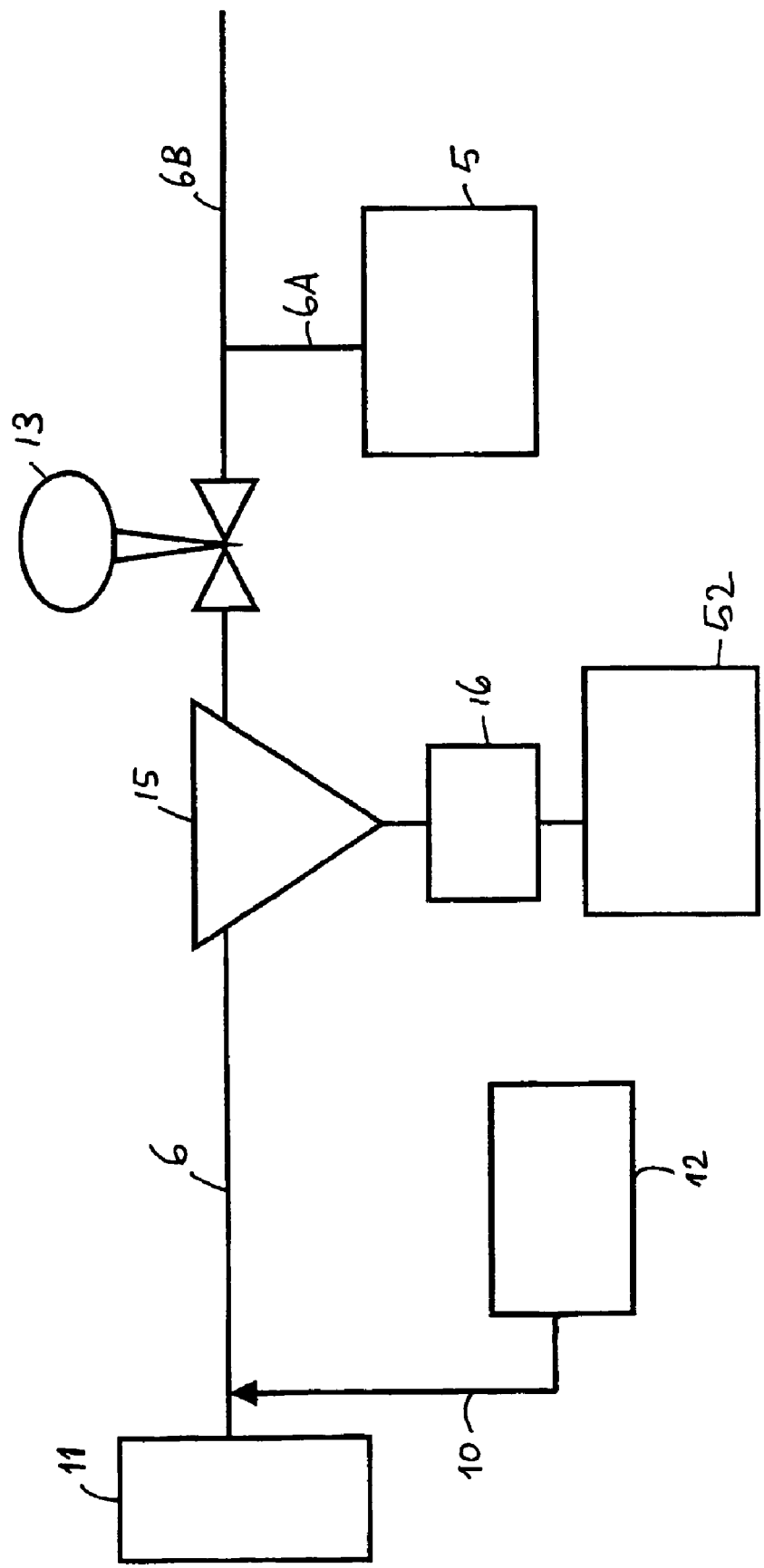

In FIG. 5, an assembly corresponding to that of FIG. 3 is shown, wherein the pressure regulator 13 is now located downstream of the gas liquid separator 15. As now the gas liquid separator is operated at a high pressure, pump 16, may now be replaced by a flow regulating device such an orifice, a capillary, a mass flow controller or a needle valve.

Figure 6:
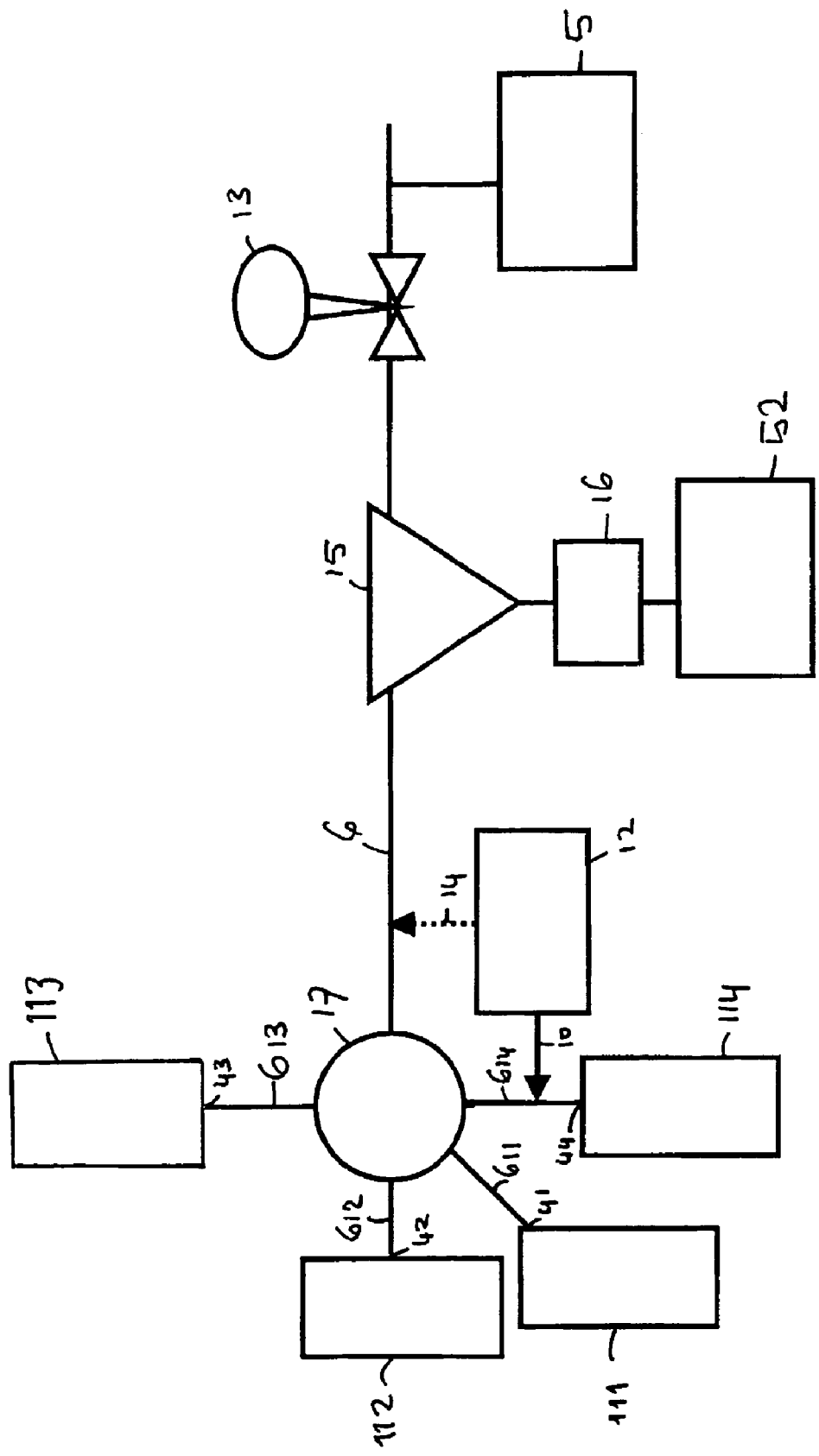
FIGS. 6, 7 and 8 show schematical diagrams of a reactor assembly according to the present invention, comprising multiple reactors, a selector valve and a sample collector.

FIG. 6 shows a reactor assembly comprising reactors 111, 112, 113 and 114, having outlets 41, 42, 43 and 44 respectively, being connected to a selector valve 17 by effluent conduits 611, 612, 613 and 614 respectively. Features already discussed in previous figures have corresponding reference numbers.

The dilution fluid supply means 10 are connected to each of the effluent conduits 611, 612, 613 and 614 of which only the connection with effluent conduit 614 is shown. Alternatively, the dilution fluid supply means can be connected to effluent conduit 6, downstream of the selector valve 17, therewith obviating the necessity for connection to each of the effluent conduits upstream of the selection valve; this indicated by dotted arrow 14. Further, effluent conduit 6 is connected to a gas/liquid separator 15 according to the assembly of FIG. 5.

Figure 7:
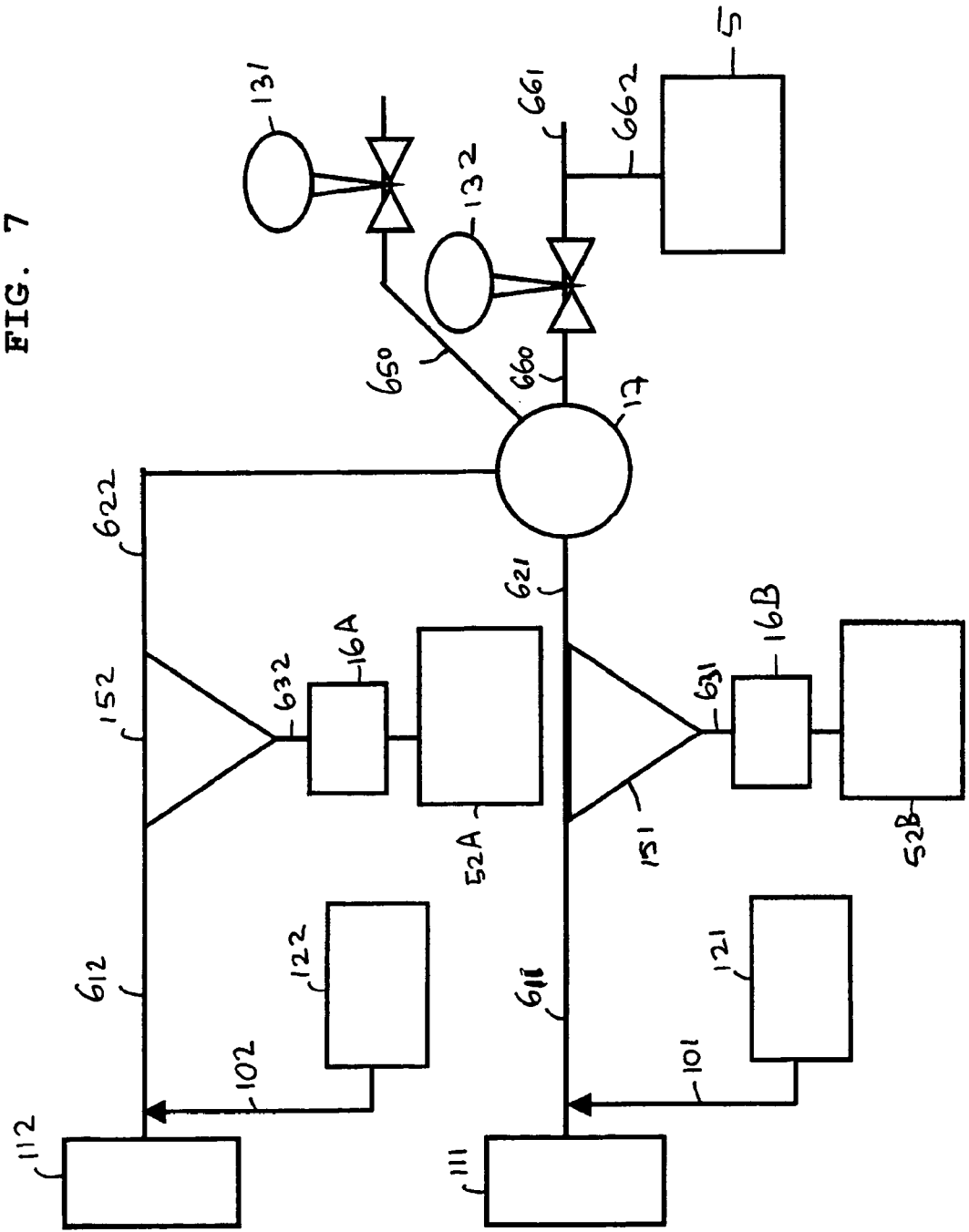

An alternative embodiment is shown in FIG. 7, wherein the assembly comprises reactors 111 and 112, each being connected to a multiple valve 17 by effluent conduits 611 and 612 respectively. Effluent conduits 611 and 612 are connected to dilution fluid supply means 101 and 102 respectively, being fed from buffer vessels 121 and 122 respectively. Preferably the buffer vessels 121 and 122 are one and the same. Dilution fluid supply means 101 and 102 may each comprise of a capillary of equal length and diameter leading to an equal flow to each effluent conduit; also other flow constricting means, known in the art may be used for this function. Effluent conduits 611 and 612 are connected each to a separate gas/liquid separator 151 and 152 respectively, the gas/liquid separator 152 separating the liquid effluent and the gaseous effluent into effluent conduits 632 and 622 respectively. Effluent conduit 622 is connected to the selector valve 17, whereas effluent conduit 632 is connected to a liquid analyser. Accordingly, effluent conduit 611 is connected to gas/liquid separator 151, separating the gaseous and liquid components of the effluent stream to effluent conduits 621 and 631 respectively. Effluent conduit 621 is connected to the selector valve, whereas effluent conduit 631 is connected to a liquid analyser. The selector valve is further connected to conduits 650 and 660, each comprising a pressure regulator 131 and 132 respectively. Conduit 660 branches, downstream of the pressure regulator 132 to conduit 661 and conduit 662. Conduit 662 is connected to a gas analyser. Those who are skilled in the art will recognise that the concept shown in FIG. 7 can easily be extrapolated to more than two reactors, by simply multiplying all the components.

Figure 8:
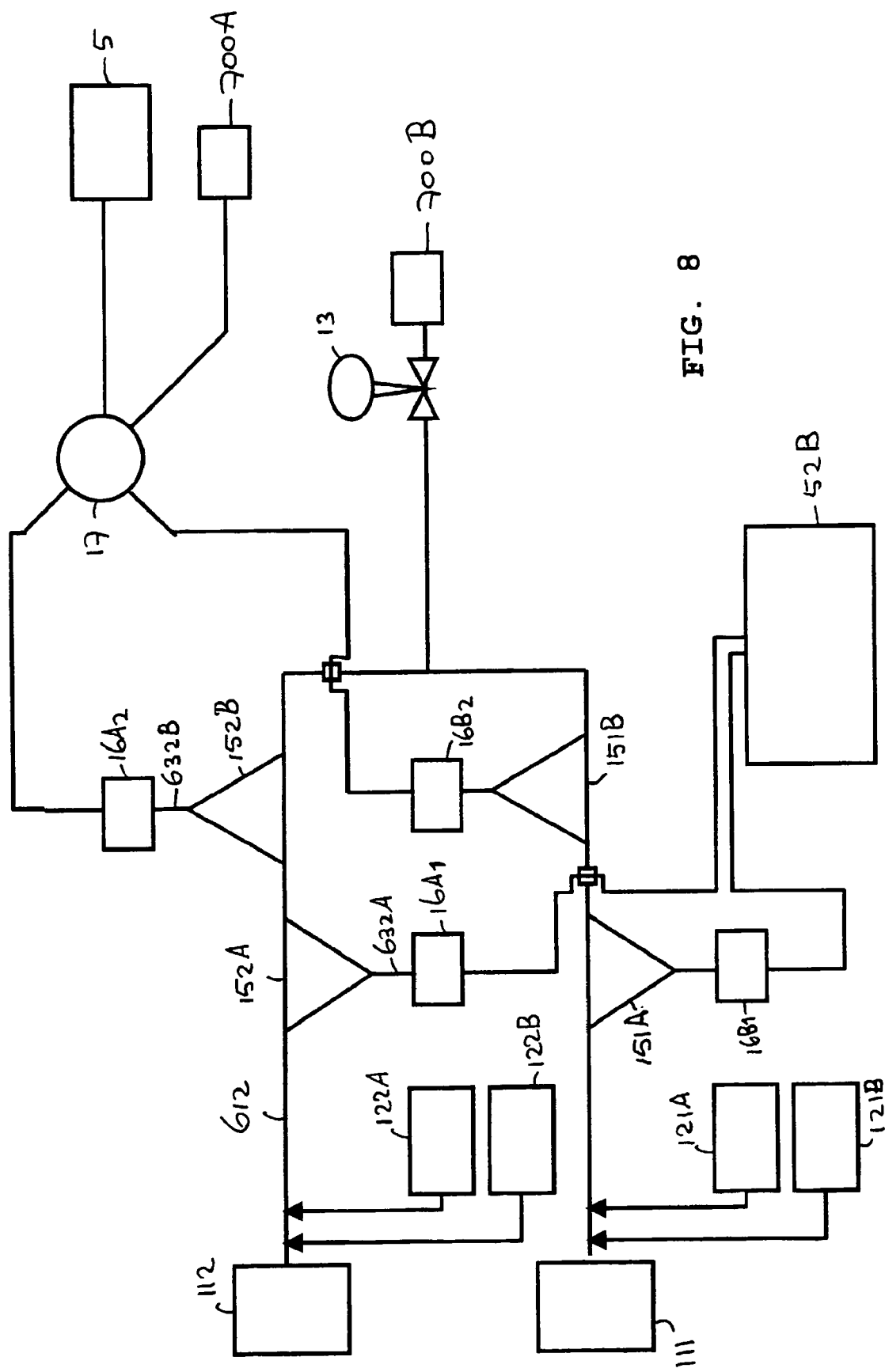

In FIG. 8, an assembly arrangement similar to that of FIG. 7 is shown, wherein however each effluent stream is connected to two serially arranged gas/liquid separators (151a, 151b and 152a, 152b respectively). In the upstream gas/liquid separators 151a and 152a, a representative amount of liquid is separated from the effluent stream and analysed by a liquid sample collector 52b. Downstream of separator 151a and 152a, separators 151b and 152b are arranged, receiving the effluent mixture comprising the gas and still also liquid of the original effluent stream. In the said separators 151b and 152b, a representative amount of gas is separated and analysed in gas analyser 5. The not separated residual effluent mixture is discarded from the assembly through vents 700a and 700b respectively.

Figure 9:
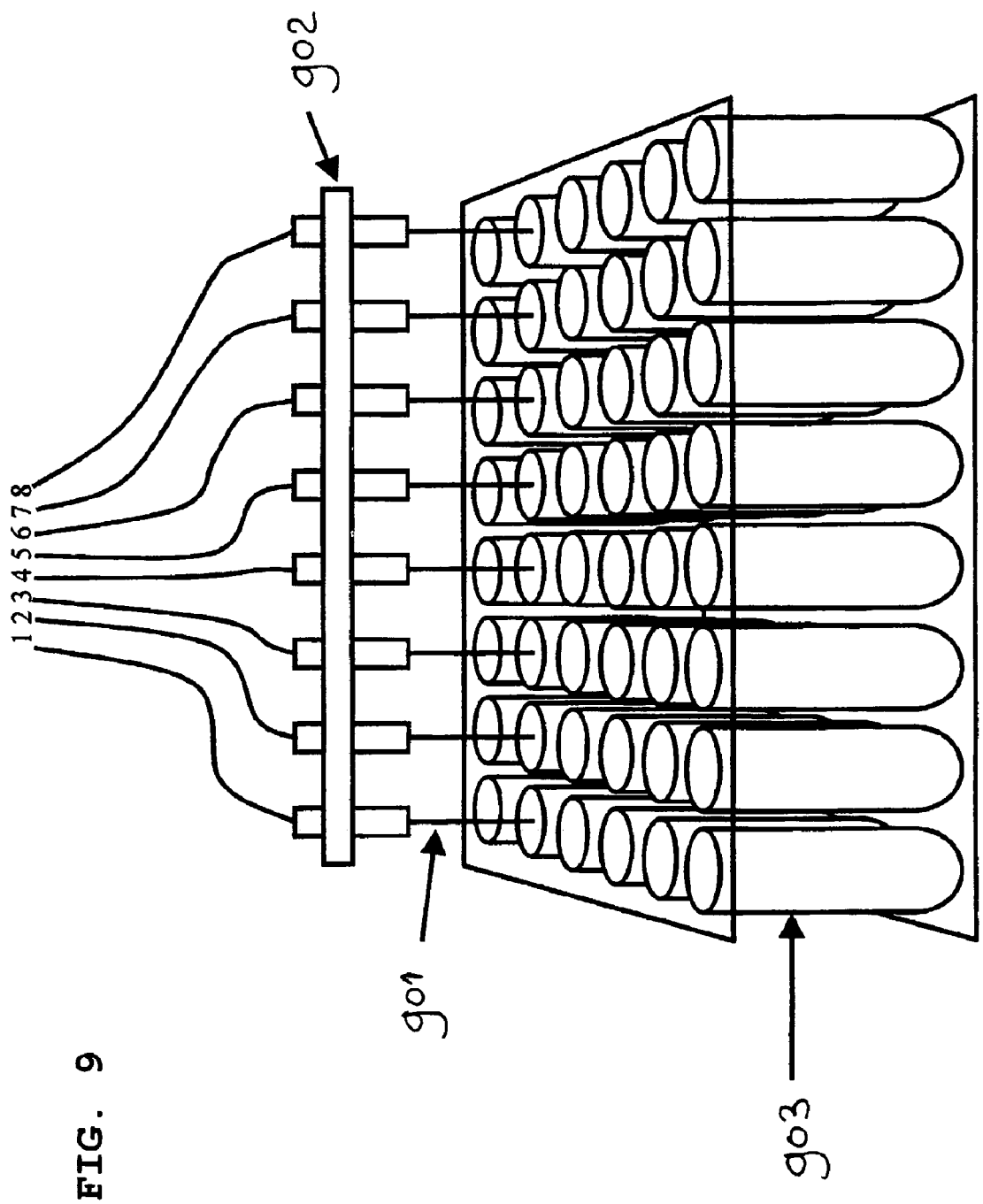

FIG. 9 shows a liquid sample collector in more detail, comprising eight conducts (1-8) for transporting the liquid to be analysed, wherein each conduct is connected to needles 901 for discharging the liquid in collection containers 903. The needles 901 are held by a robot arm 902 that can be automatically or manually moved, so that the liquid, dispensed from a needle, can be dispensed in a plurality of containers 903.

Referring to the above figures, the action of the assembly according to the present invention as well as the method of the invention will be further explained.

Referring to FIG. 1, a fluid inflow, comprising at least one reactant is entered in the reaction chamber and is subjected to a chemical reaction in the reaction zone 2. As the effluent stream from the reaction zone enters the space 7 in the reaction chamber 1, downstream of the reaction zone, the said effluent stream is contacted with the dilution fluid, introduced into the said space by the dilution fluid supply means 10. In space 8, mixing/dilution of the effluent stream in the dilution fluid takes place, where upon the mixture/dilution is further transferred to the analyser 5 through effluent conduit 6. In case the dilution fluid supply means are connected to the effluent conduit 6 and not discharging in the reaction chamber, the effluent stream is contacted with the dilution fluid in the effluent conduit. In order to obtain proper mixing, the effluent conduit may comprise mixing elements, such as static mixing elements, however, the effluent stream and the dilution fluid can be contacted to one another and mixed without the aid of mixing devices. The effluent conduit may comprise a back-pressure regulator, as is shown in FIG. 2. Downstream or upstream of the pressure regulator, a gas/liquid separator can be present in the effluent conduit, separating the gaseous components of the effluent conduit from the liquid components thereof. The liquid components are transferred to liquid analyser 52 with the aid of a pump 16. However, any other device known in the art can be used for transport of the liquid from the gas/liquid separator 15 to the liquid analyser 52. In a special embodiment, the conduit connecting the gas/liquid separator and the liquid analyser comprises a capillary. This configuration is highly suitable when operating at elevated pressures. Due to the pressure difference over the capillary a small stream of liquid will be created exiting the gas/liquid separator and entering the liquid analyser. The capillary system has the advantage that is low cost, easy to install and highly robust, allowing it to operate at very high pressures.

As indicated before, the liquid analyser may also comprise of a sample collection system, such as a parallel sample collector, as described above and further illustrated in FIG. 9.

The gaseous components of the effluent are further transferred to a gas analyser 5. Any surplus of gaseous components may be discarded via conduit 6b. However, said conduit may also be connected to a second gas analyser. In the multi-reactor configuration of FIG. 6, multiple reactors 111-114 are connected, via a selector valve and a gas/liquid separator to the analysers, analysing the effluent streams of the respective reactors. In order to analyse the different effluent streams, originating from the different reactors, the selector valve connects one of the effluent conduits 611-614 to conduit 6, therewith blocking passage of the effluent streams from the other effluent conduits to conduit 6. As indicated above, the effluent stream is diluted either in the conduit connecting the reactor to the selector valve (conduit 611-614) or in conduit 6. The effluent stream, passing through the selector valve can be analysed as indicated above by a liquid analyser 52 and a gas analyser 5. After proper analyses, the connection between one of the effluent conduits 611-614 and conduit 6 is closed by the selector valve and another effluent conduit, originating from a following reactor is connected to conduit 6, therewith enabling analyses of the effluent stream, originating from the said reactor. This process can be repeated until all effluent streams are analysed. If desired, multiple analyses of each reactor can be performed. The effluent streams of reactors, that are blocked by the selector valve are led to a waste outlet (not shown). The skilled person will be aware of proper choice and positioning of such a waste outlet.

The selector valve can also be positioned in the reactor assembly after separation of the gaseous from the liquid components from the effluent streams. In the arrangement, shown in FIG. 7, the selector valve is connected to conduits, transferring gaseous components from different reactors to the gas analyser. The gas/liquid separation and analysis of liquid components is performed upstream of the said selector valve by gas/liquid separators 151 and 152, and sample collectors 52A and 52B respectively; however, it is also possible to introduce an additional selector valve, connecting e.g. conduits 631 and 632 for liquid components of the different effluent streams, to a single liquid analyser, connected downstream to the said second selector valve.

It is also possible to connect outlets 631 and 632 to a parallel sample collection system allowing simultaneous collection of the diluted selection stream.

In FIG. 8, the effluent stream from reactor 111 enters gas/liquid separator 151a, wherein a representative portion of the liquid effluent stream is separated and passed to liquid sample collector 52b. The gaseous effluent stream, possibly still containing a portion of the liquid components of the effluent stream (not separated by the separator 151a) enters gas/liquid separator 151b, wherein a representative portion of the gaseous components of the effluent stream are separated and passed to gas analyser 5 via multi selector valve 17. Not separated residual effluent mixture is passed to vent 700b. Accordingly, the effluent stream from reactor 112 is passed to gas/liquid separators 152a and 152b respectively, whereas the not separated residual effluent mixture thereof is discarded through vent 700a. In this arrangement, gas/liquid separators of a relatively simple design can be used, as the gaseous/liquid mixture of the effluent stream does not have to be completely separated in a quantitative manner, as indicated above.

EXAMPLES

The reduction of 3-hexen-2-on to 3-hexen-2-ol was performed both in gas phase as in trickle flow mode. A fixed reaction pressure of 10 bar and a reaction temperature of 100° C. was chosen in both cases. The saturated vapour pressure of 3-hexen-2-ol at 100° C. is approximately 20 kPa and at 25° C. it is 0.3 kPa.

Example: 1 Reduction of 3-hexen-2-on to 3-hexen-2-ol in the Gas Phase

The reactor set-up as shown in FIG. 1e and FIG. 7 without however the presence of a gas/liquid separator and a liquid analyser. The equipment was equipped 64 reactors in parallel with one GC.

A library of heterogeneous catalysts with a wide variation in chemical composition was loaded in the reactors. The amount of catalyst was 100 µg per individual reactor. 5 Nml/min/reactor (0.2 mmol/min/reactor) of hydrogen gas and 0.004 mmol/min 3-hexen-2-on liquid feed was fed to each reactor. Thus the gas in the reaction zone may just consist of 2 v % 3-hexen-2-ol.

The reaction mixture flowing out of the reactor was led through traced lines to the GC analyser. To increase speed to the analyzer and prevent condensation the reactor mixture exiting the reaction zone was diluted with 50 Nml/min/reactor nitrogen, where the gas was added according to FIG. 1E. To measure all reaction mixtures rotary selection valves are used. For accurate measurements internal and external standards were used. 1 v % of helium (internal standard 1) was fed together with the hydrogen and 1 v % of cyclohexane (internal standard 2) was fed together with the 3-hexen-2-on.

The GC peaks were integrated and the ratio between the individual components and the internal standards were calculated. From this the production rate and the conversion, selectivity and yield could be calculated. See table 1.

Example 2: Reduction of 3-hexen-2-on to 3-hexen-2-ol in the Trickle Phase

By adding significantly more 3-hexen-2-on the majority of the reactant will remain in the liquid phase, causing the reactant to trickle through the catalyst bed. The term "trickle phase" means that a mixture of gas and liquid is fed to a reaction zone, wherein the liquid passes (trickles) through the said zone by gravity force. In this experiment a 3-hexen-2-on feed of 0.083 mmole/min/reactor (20 times more then in the preceding example) was used. To the outlet of each reactor di-isopropylether diluent was added at 100 mg/min/reactor using a pump and a distributor with capillaries. The diluent contained 0.0.085 mole % of hexadecane internal standard. The hexadecane flow rate was 0.83 micromole/min. To the liquid reactor feed also 1 vol % heptadecane was added as an internal standard. This internal standard together with the hexadecane standard allows us to monitor the ratio of the reactant flow rate and the diluent flow rate for each individual reactor. Also a gas diluent was added consisting of 10 Nml/min/reactor nitrogen with 0.44 vol % of He.

For the liquid diluent addition, gas diluent addition and gas/liquid separation a set-up was used as described in FIGS. 1E, 8 and 9. The gas/liquid separator has a dimension of approximately 0.5 ml, which gives a good separation in a gas/liquid stream and a liquid stream. The separation block with the gas/liquid separators was cooled to room temperature to optimise gas/liquid separation. The liquid stream was collected with a robotic fraction collector in GC vials, for later off-line analysis. The system resembles the system of FIG. 9 but then 64 outlets were used instead of 8. Every hour 64 new GC vials were placed under the liquid effluent outlet.

The gas/liquid stream from the separator flows to the selection valves. The selected stream is then led over a second gas liquid separator, which separates the selected stream in a gas-liquid and a gas flow. Then the pressure of the remaining gas flow is reduced to atmospheric pressure from which the online GC takes samples.

The GC peaks of both the liquid phase and the gas phase were integrated and the ratio between the individual components and the internal standards were calculated. From this the production rate and the conversion, selectivity and yield could be calculated. See table 2.

TABLE 1

| Reactor number (—) | Catalyst (—) | Time measured (hr:min) | Concentration relative to internal standard | | | | | Calculated catalyst performance | | | | |
|---|---|---|---|---|---|---|---|---|---|---|---|---|
| | | | C6H10O 3-hexen-2on (mol/mol (I)st) | C6H11OH 3-hexen-2-ol (mol/mol (I)st) | C6H13OH 3-hexanol (mol/mol (I)st) | C6H14 hexane (mol/mol (I)st) | H2 (mol/mol (g)st) | C6H10O conversion (%) | C6H11OH yield (%) | C6H13OH yield (%) | C6H14 yield (%) | C6H11OH selectivity (%) |
| 1 | AVCat1 | 09:00 | 111.80 | 2.58 | 0.50 | 0.00 | 101.14 | 3.0 | 2.2 | 0.4 | 0.0 | 73.7 |
| 2 | AVCat2 | 09:10 | 17.49 | 59.67 | 37.13 | −0.29 | 98.68 | 84.8 | 51.8 | 32.2 | −0.3 | 61.0 |
| 3 | AVCat3 | 09:20 | 25.45 | 20.05 | 22.58 | 46.44 | 97.61 | 77.9 | 17.4 | 19.5 | 40.3 | 22.3 |
| 4 | AVCat4 | 09:30 | 108.90 | 7.01 | 0.57 | −1.04 | 101.11 | 7.3 | 6.1 | 0.5 | −0.9 | 83.5 |
| 5 | AVCat5 | 09:40 | 91.91 | 11.31 | 3.88 | 6.80 | 100.51 | 20.3 | 9.8 | 3.4 | 5.9 | 48.3 |
| 6 | AVCat6 | 09:50 | 67.97 | 48.46 | 0.43 | 0.00 | 100.37 | 41.0 | 40.3 | 0.4 | 0.0 | 98.2 |
| 7 | AVCat7 | 10:00 | 109.99 | 4.13 | 0.07 | 0.00 | 101.13 | 4.6 | 3.6 | 0.1 | 0.0 | 77.7 |
| 8 | AVCat8 | 10:10 | 25.54 | 35.93 | 0.95 | 51.44 | 97.83 | 77.9 | 31.2 | 0.8 | 44.6 | 40.0 |
| 9 | AVCat9 | 10:20 | 84.71 | 21.67 | 5.87 | 1.41 | 100.54 | 29.5 | 18.8 | 5.1 | 1.2 | 70.8 |
| 10 | AVCat10 | 10:30 | 45.03 | 47.33 | 18.15 | 4.25 | 99.51 | 60.9 | 41.0 | 15.7 | 3.7 | 67.4 |
| 11 | AVCat11 | 10:40 | 102.90 | 2.65 | 3.48 | 4.57 | 100.79 | 10.8 | 2.3 | 3.0 | 4.0 | 21.3 |
| 12 | AVCat12 | 10:50 | 69.78 | 3.41 | 20.66 | 2.25 | 99.69 | 39.5 | 3.0 | 32.9 | 1.9 | 7.5 |
| 13 | AVCat13 | 11:00 | 25.82 | 73.58 | 11.20 | 3.21 | 99.35 | 77.6 | 63.8 | 9.7 | 2.8 | 82.2 |
| 14 | AVCat14 | 11:10 | 43.12 | 68.08 | 0.94 | 2.46 | 99.84 | 62.6 | 59.0 | 0.8 | 2.1 | 94.3 |
| 15 | AVCat15 | 11:20 | 103.60 | 2.67 | 7.35 | 0.00 | 100.90 | 10.2 | 2.3 | 6.4 | 0.0 | 22.8 |
| 16 | AVCat16 | 11:30 | 39.19 | 24.68 | 8.07 | 41.47 | 98.30 | 66.0 | 21.4 | 7.0 | 36.0 | 32.4 |
| 17 | AVCat17 | 11:40 | 71.77 | 2.41 | 40.98 | 0.00 | 99.72 | 37.8 | 2.1 | 35.5 | 0.0 | 5.5 |
| 18 | AVCat18 | 11:50 | 110.51 | 2.87 | 0.34 | 1.37 | 101.07 | 4.2 | 2.5 | 0.3 | 1.2 | 60.0 |
| 19 | AVCat19 | 12:00 | 38.17 | 23.55 | 18.47 | 34.84 | 98.30 | 68.9 | 20.4 | 16.0 | 30.2 | 30.5 |
| 20 | AVCat20 | 12:10 | 41.41 | 8.49 | 20.66 | 44.41 | 97.99 | 64.1 | 7.4 | 17.9 | 38.5 | 11.5 |
| 21 | AVCat21 | 12:20 | 40.34 | 7.93 | 43.57 | 21.74 | 98.39 | 65.0 | 6.9 | 37.8 | 18.9 | 10.6 |
| 22 | AVCat22 | 12:30 | 39.95 | 20.13 | 23.61 | 31.22 | 98.37 | 65.3 | 17.5 | 20.5 | 27.1 | 26.7 |
| 23 | AVCat23 | 12:40 | 84.00 | 28.60 | 1.86 | −0.49 | 100.68 | 27.1 | 24.8 | 1.6 | −0.4 | 91.4 |
| 24 | AVCat24 | 12:50 | 8.36 | 33.88 | 60.96 | 10.36 | 97.92 | 92.7 | 29.4 | 52.9 | 9.0 | 31.7 |
| 25 | AVCat25 | 13:00 | 101.35 | 8.33 | 0.30 | 4.27 | 100.82 | 12.1 | 7.2 | 0.3 | 3.7 | 59.7 |
| 26 | AVCat26 | 13:10 | 112.13 | 2.64 | 0.36 | −0.87 | 101.19 | 2.8 | 2.3 | 0.3 | −0.8 | 83.0 |
| 27 | AVCat27 | 13:20 | 14.44 | 40.08 | 53.17 | 6.91 | 98.27 | 87.5 | 34.7 | 46.1 | 6.0 | 39.7 |
| 28 | AVCat28 | 13:30 | 36.84 | 0.37 | 30.72 | 46.58 | 97.66 | 68.1 | 0.3 | 26.6 | 40.4 | 0.5 |
| 29 | AVCat29 | 13:40 | 14.52 | 74.97 | 19.81 | 5.59 | 98.89 | 87.4 | 65.0 | 17.2 | 4.8 | 74.4 |
| 30 | AVCat30 | 13:50 | 7.52 | 6.44 | 13.46 | 86.23 | 96.07 | 93.5 | 5.6 | 11.7 | 74.8 | 6.0 |
| 31 | AVCat31 | 14:00 | 29.19 | 78.16 | 3.34 | 4.53 | 99.47 | 74.7 | 67.8 | 2.9 | 3.9 | 90.8 |
| 32 | AVCat32 | 14:10 | 49.74 | 45.93 | 7.17 | 11.67 | 99.52 | 56.9 | 39.8 | 6.2 | 10.3 | 70.1 |
| 33 | AVCat33 | 14:20 | 50.45 | 28.70 | 19.17 | 15.62 | 99.21 | 56.2 | 24.9 | 16.6 | 13.5 | 44.3 |
| 34 | AVCat34 | 14:30 | 2.15 | 10.41 | 43.79 | 57.69 | 96.44 | 98.1 | 9.0 | 38.0 | 50.0 | 9.2 |
| 35 | AVCat35 | 14:40 | 93.77 | 16.27 | 2.92 | 1.76 | 100.72 | 18.7 | 14.1 | 2.5 | 1.5 | 75.6 |
| 36 | AVCat36 | 14:50 | 105.24 | 7.40 | 0.88 | 0.98 | 100.99 | 8.7 | 6.4 | 0.8 | 0.9 | 73.6 |
| 37 | AVCat37 | 15:00 | 47.45 | 65.71 | 1.06 | −0.82 | 100.05 | 58.8 | 57.0 | 0.9 | −0.7 | 96.8 |
| 38 | AVCat38 | 15:10 | 14.04 | 28.05 | 28.58 | 44.04 | 97.38 | 87.8 | 24.3 | 24.8 | 38.2 | 27.7 |
| 39 | AVCat39 | 15:20 | 90.93 | 4.19 | 5.64 | 12.60 | 100.26 | 21.1 | 3.6 | 4.9 | 10.9 | 17.2 |
| 40 | AVCat40 | 15:30 | 84.04 | 5.63 | 8.25 | 15.77 | 99.98 | 27.1 | 4.9 | 7.2 | 13.7 | 18.0 |
| 41 | AVCat41 | 15:40 | 75.76 | 0.09 | 27.83 | 9.79 | 99.71 | 34.3 | 0.1 | 24.1 | 8.5 | 0.2 |
| 42 | AVCat42 | 15:50 | 95.26 | 2.44 | 9.73 | 6.31 | 100.48 | 17.4 | 2.1 | 8.4 | 5.5 | 12.2 |
| 43 | AVCat43 | 16:00 | 79.50 | 15.89 | 3.36 | 15.24 | 100.00 | 31.1 | 13.8 | 2.9 | 13.2 | 44.4 |
| 44 | AVCat44 | 16:10 | 81.94 | 24.83 | 6.78 | 0.00 | 100.53 | 28.9 | 21.5 | 5.9 | 0.0 | 74.4 |

TABLE 1-continued

| Reactor number (—) | Catalyst (—) | Time measured (hr min) | Concentration relative to internal standard | | | | | | Calculated catalyst performance | | | | |
|---|---|---|---|---|---|---|---|---|---|---|---|---|---|
| | | | C6H10O 3-hexen-2on (mol/mol (I)st) | C6H11OH 3-hexen-2-ol (mol/mol (I)st) | C6H13OH 3-hexanol (mol/mol (I)st) | C6H14 hexane (mol/mol (I)st) | H2 (mol/mol (g)st) | C6H10O conversion (%) | C6H11OH yield (%) | C6H13OH yield (%) | C6H14 yield (%) | C6H11OH selectivity (%) |
| 45 | AVCat45 | 16:20 | 89.03 | 14.37 | 11.10 | 0.48 | 100.53 | 22.8 | 12.5 | 9.6 | 0.4 | 54.7 |
| 46 | AVCat46 | 16:30 | 0.12 | 55.15 | 4.44 | 53.61 | 97.25 | 99.9 | 47.8 | 3.9 | 46.5 | 47.9 |
| 47 | AVCat47 | 16:40 | 11.67 | 49.15 | 47.95 | 5.99 | 98.34 | 89.9 | 42.6 | 41.6 | 5.2 | 47.4 |
| 48 | AVCat48 | 16:50 | 71.93 | 17.60 | 2.83 | 20.94 | 99.69 | 37.6 | 15.3 | 2.5 | 18.2 | 40.6 |
| 49 | AVCat49 | 17:00 | 47.74 | 58.49 | 8.16 | 0.26 | 99.87 | 58.6 | 50.7 | 7.1 | 0.2 | 86.6 |
| 50 | AVCat50 | 17:10 | 107.24 | 5.11 | 1.07 | 0.97 | 101.02 | 7.0 | 4.4 | 0.9 | 0.8 | 63.4 |
| 51 | AVCat51 | 17:20 | 103.15 | 6.23 | 0.16 | 4.89 | 100.83 | 10.5 | 5.4 | 0.1 | 4.2 | 51.3 |
| 52 | AVCat52 | 17:30 | 48.55 | 58.59 | 3.65 | 3.59 | 99.65 | 57.9 | 50.8 | 3.2 | 3.1 | 87.8 |
| 53 | AVCat53 | 17:40 | 56.44 | 2.03 | 16.49 | 39.61 | 98.50 | 51.0 | 1.8 | 14.3 | 34.4 | 3.4 |
| 54 | AVCat54 | 17:50 | 50.26 | 28.91 | 5.45 | 30.00 | 98.92 | 56.4 | 25.1 | 4.7 | 26.0 | 44.4 |
| 55 | AVCat55 | 18:00 | 25.31 | 67.58 | 12.49 | 8.20 | 99.14 | 78.1 | 58.6 | 10.8 | 7.1 | 75.1 |
| 56 | AVCat56 | 18:10 | 6.46 | 45.82 | 39.14 | 21.97 | 97.86 | 94.4 | 39.7 | 33.9 | 19.1 | 42.1 |
| 57 | AVCat57 | 18:20 | 37.33 | 12.01 | 17.93 | 47.63 | 97.85 | 67.6 | 10.4 | 15.6 | 41.3 | 15.4 |
| 58 | AVCat58 | 18:30 | 69.85 | 39.20 | 0.61 | 4.33 | 100.26 | 39.4 | 34.0 | 0.5 | 3.8 | 86.3 |
| 59 | AVCat59 | 18:40 | 96.66 | 16.41 | 1.48 | −1.19 | 100.92 | 16.2 | 14.2 | 1.3 | −1.0 | 88.0 |
| 60 | AVCat60 | 18:50 | 31.97 | 28.52 | 13.50 | 40.43 | 98.10 | 72.3 | 24.7 | 11.7 | 35.1 | 34.2 |
| 61 | AVCat61 | 19:00 | 100.15 | 12.18 | 0.36 | 1.14 | 100.91 | 13.1 | 10.6 | 0.3 | 1.0 | 80.4 |
| 62 | AVCat62 | 19:10 | 79.03 | 4.06 | 32.10 | 0.00 | 100.00 | 31.5 | 3.5 | 27.8 | 0.0 | 11.2 |
| 63 | AVCat63 | 19:20 | 85.42 | 3.68 | 9.39 | 16.46 | 99.94 | 25.9 | 3.2 | 8.1 | 14.3 | 12.3 |
| 64 | none | 19:30 | 115.30 | 0.00 | 0.00 | 0.00 | 101.20 | 0.0 | 0.0 | 0.0 | 0.0 | — |

TABLE 2

| Reactor number (−) | Catalyst (−) | Time measured (hr:min) | Concentration relative to internal standard | | | | | Calculated performance | | | | |
|---|---|---|---|---|---|---|---|---|---|---|---|---|
| | | | H2 (mol/mol (g)st) | C6H10O 3-hexen-2on (mol/mol (I)st2) | C6H11OH 3-hexen-2-ol (mol/mol (I)st2) | C6H13OH 3-hexanol (mol/mol (I)st2) | C6H14 hexane (mol/mol (I)st2) | C6H10O conversion (%) | C6H11OH yield (%) | C6H13OH yield (%) | C6H14 yield (%) | C6H11OH selectivity (%) |
| 1 | AVCat65 | 09:00 | 92.42 | 92.06 | 0.41 | 2.16 | 5.37 | 7.9 | 0.4 | 2.2 | 5.4 | 5.2 |
| 2 | AVCat66 | 09:10 | 11.88 | 3.80 | 31.56 | 12.51 | 51.13 | 96.2 | 31.6 | 13.5 | 51.1 | 32.8 |
| 3 | AVCat67 | 09:20 | 58.91 | 58.35 | 11.17 | 2.18 | 28.27 | 41.6 | 11.2 | 2.2 | 28.3 | 26.8 |
| 4 | AVCat68 | 09:30 | 17.24 | 15.47 | 9.47 | 35.41 | 39.65 | 84.5 | 9.5 | 35.4 | 39.6 | 11.2 |
| 5 | AVCat69 | 09:40 | 90.31 | 87.65 | 2.21 | 6.17 | 3.77 | 12.1 | 2.2 | 8.2 | 3.8 | 18.2 |
| 6 | AVCat70 | 09:50 | 76.22 | 42.96 | 55.61 | 0.23 | 1.01 | 57.0 | 55.8 | 0.2 | 1.0 | 97.8 |
| 7 | AVCat71 | 10:00 | 62.34 | 37.42 | 39.52 | 16.46 | 6.60 | 82.6 | 39.3 | 15.3 | 5.5 | 63.2 |
| 8 | AVCat72 | 10:10 | 24.15 | 6.04 | 21.24 | 56.56 | 18.16 | 94.0 | 21.2 | 56.6 | 16.2 | 22.6 |
| 9 | AVCat73 | 10:20 | 98.72 | 97.25 | 0.04 | 2.29 | 0.42 | 2.8 | 0.0 | 2.3 | 0.4 | 1.4 |
| 10 | AVCat74 | 10:30 | 93.99 | 13.08 | 3.88 | 5.00 | 1.08 | 86.9 | 3.9 | 5.0 | 1.1 | 4.5 |
| 11 | AVCat75 | 10:40 | 84.93 | 61.98 | 37.46 | 0.55 | 0.01 | 38.0 | 37.5 | 0.5 | 0.0 | 98.5 |
| 12 | AVCat76 | 10:50 | 64.15 | 55.23 | 8.70 | 28.99 | 7.08 | 44.8 | 8.7 | 29.0 | 7.1 | 19.4 |
| 13 | AVCat77 | 11:00 | 51.95 | 23.15 | 42.03 | 29.63 | 5.19 | 76.9 | 42.0 | 29.6 | 5.2 | 54.7 |
| 14 | AVCat78 | 11:10 | 30.66 | 30.47 | 24.67 | 39.31 | 5.55 | 69.5 | 24.7 | 39.3 | 5.5 | 35.5 |
| 15 | AVCat79 | 11:20 | 31.68 | 1.10 | 15.38 | 60.60 | 9.46 | 98.9 | 15.4 | 60.6 | 9.5 | 15.6 |
| 16 | AVCat80 | 11:30 | 65.03 | 65.15 | 0.01 | 18.68 | 16.16 | 34.6 | 0.0 | 18.7 | 16.2 | 0.0 |
| 17 | AVCat81 | 11:40 | 72.19 | 37.29 | 59.36 | 0.56 | 2.79 | 62.7 | 59.4 | 0.6 | 2.8 | 94.7 |
| 18 | AVCat82 | 11:50 | 78.46 | 73.46 | 3.03 | 19.58 | 3.93 | 26.5 | 3.0 | 18.6 | 3.9 | 11.4 |
| 19 | AVCat83 | 12:00 | 85.59 | 73.22 | 21.64 | 0.03 | 5.12 | 26.8 | 21.6 | 0.0 | 5.1 | 60.8 |
| 20 | AVCat84 | 12:10 | 84.00 | 75.20 | 13.08 | 7.44 | 4.28 | 24.8 | 13.1 | 7.4 | 4.3 | 52.7 |
| 21 | AVCat85 | 12:20 | 88.87 | 82.50 | 8.98 | 8.98 | 1.44 | 17.4 | 7.0 | 9.0 | 1.4 | 40.1 |
| 22 | AVCat86 | 12:30 | 59.37 | 42.86 | 33.95 | 4.28 | 18.94 | 57.1 | 33.9 | 4.3 | 18.9 | 59.4 |
| 23 | AVCat87 | 12:40 | 92.24 | 87.66 | 6.73 | 1.72 | 3.70 | 12.1 | 6.7 | 1.7 | 3.7 | 55.4 |
| 24 | AVCat88 | 12:50 | 94.75 | 92.56 | 0.59 | 5.85 | 1.01 | 7.4 | 0.6 | 5.8 | 1.0 | 8.0 |
| 25 | AVCat89 | 13:00 | −1.82 | 13.85 | 5.28 | 3.43 | 77.45 | 88.2 | 5.3 | 3.4 | 77.4 | 6.1 |
| 26 | AVCat90 | 13:10 | 82.47 | 62.82 | 30.68 | 5.72 | 0.78 | 37.2 | 30.7 | 5.7 | 0.8 | 82.5 |
| 27 | AVCat91 | 13:20 | 55.91 | 7.58 | 83.38 | 3.12 | 5.96 | 92.4 | 83.4 | 3.1 | 6.0 | 90.2 |
| 28 | AVCat92 | 13:30 | 78.69 | 82.92 | 25.33 | 7.15 | 4.60 | 37.1 | 25.3 | 7.2 | 4.6 | 68.3 |
| 29 | AVCat93 | 13:40 | 7.86 | 4.04 | 30.29 | 5.88 | 59.83 | 96.0 | 30.3 | 5.9 | 59.8 | 31.5 |
| 30 | AVCat94 | 13:50 | 63.01 | 41.88 | 28.60 | 26.52 | 2.99 | 58.1 | 28.6 | 26.5 | 3.0 | 49.2 |
| 31 | AVCat95 | 14:00 | 93.77 | 89.88 | 6.34 | 0.05 | 3.73 | 10.1 | 8.3 | 0.1 | 3.7 | 62.6 |
| 32 | AVCat96 | 14:10 | 64.57 | 58.45 | 13.48 | 11.00 | 17.07 | 41.8 | 13.5 | 11.0 | 17.1 | 32.4 |
| 33 | AVCat97 | 14:20 | 72.38 | 63.69 | 17.80 | 4.93 | 13.57 | 36.3 | 17.8 | 4.9 | 13.6 | 49.0 |
| 34 | AVCat98 | 14:30 | 37.27 | 2.30 | 52.90 | 35.58 | 9.22 | 97.7 | 52.9 | 35.6 | 9.2 | 54.1 |
| 35 | AVCat99 | 14:40 | 81.47 | 68.45 | 19.10 | 9.65 | 2.81 | 31.6 | 19.1 | 9.6 | 2.8 | 60.5 |
| 36 | AVCat100 | 14:50 | 17.36 | 18.86 | 8.80 | 26.86 | 45.48 | 81.1 | 8.8 | 25.9 | 45.5 | 10.8 |
| 37 | AVCat101 | 15:00 | 48.33 | 42.91 | 20.43 | 0.20 | 36.47 | 57.1 | 20.4 | 0.2 | 36.5 | 35.8 |
| 38 | AVCat102 | 15:10 | 66.28 | 32.68 | 54.43 | 10.24 | 2.65 | 67.3 | 54.4 | 10.2 | 2.7 | 80.9 |
| 39 | AVCat103 | 15:20 | 87.71 | 70.28 | 19.08 | 4.75 | 5.89 | 29.7 | 19.1 | 4.8 | 5.9 | 64.2 |
| 40 | AVCat104 | 15:30 | 43.64 | 25.99 | 38.43 | 8.58 | 27.00 | 74.0 | 38.4 | 8.6 | 27.0 | 51.9 |
| 41 | AVCat105 | 15:40 | 48.72 | 34.12 | 25.83 | 21.44 | 18.60 | 65.9 | 25.8 | 21.4 | 18.6 | 39.2 |
| 42 | AVCat106 | 15:50 | 56.25 | 29.83 | 48.28 | 11.77 | 10.04 | 70.1 | 48.3 | 11.8 | 10.0 | 68.9 |
| 43 | AVCat107 | 16:00 | 55.71 | 29.50 | 48.25 | 11.03 | 13.21 | 70.5 | 48.2 | 11.0 | 13.2 | 65.6 |
| 44 | AVCat108 | 16:10 | 55.41 | 22.73 | 55.50 | 12.15 | 9.62 | 77.3 | 55.5 | 12.1 | 9.6 | 71.8 |

TABLE 2-continued

| Reactor number (—) | Catalyst (—) | Time measured (hr min) | H2 (mol/mol (g)st) | Concentration relative to internal standard | | | | C6H10O conversion (%) | Calculated performance | | | C6H11OH selectivity (%) |
| --- | --- | --- | --- | --- | --- | --- | --- | --- | --- | --- | --- | --- |
| | | | | C6H10O 3-hexen-2on (mol/mol (I)st2) | C6H11OH 3-hexen-2-ol (mol/mol (I)st2) | C6H13OH 3-hexanol (mol/mol (I)st2) | C6H14 hexane (mol/mol (I)st2) | | C6H11OH yield (%) | C6H13OH yield (%) | C6H14 yield (%) | |
| 45 | AVCat109 | 16:20 | 44.89 | 33.45 | 29.82 | 6.38 | 30.35 | 68.5 | 29.8 | 6.4 | 30.4 | 44.8 |
| 46 | AVCat110 | 16:30 | 50.14 | 5.35 | 78.75 | 5.27 | 10.63 | 94.6 | 78.7 | 5.3 | 10.6 | 83.2 |
| 47 | AVCat111 | 16:40 | 76.29 | 42.16 | 57.10 | 0.21 | 0.53 | 57.8 | 57.1 | 0.2 | 0.5 | 98.7 |
| 48 | AVCat112 | 16:50 | 50.12 | 43.09 | 6.44 | 36.85 | 13.82 | 56.9 | 6.4 | 36.7 | 13.8 | 11.3 |
| 49 | AVCat113 | 17:00 | 93.99 | 91.65 | 0.79 | 6.37 | 1.20 | 8.4 | 0.8 | 6.4 | 1.2 | 9.4 |
| 50 | AVCat114 | 17:10 | 55.13 | 48.98 | 7.07 | 29.61 | 14.34 | 51.0 | 7.1 | 29.6 | 14.3 | 13.9 |
| 51 | AVCat115 | 17:20 | 65.17 | 50.13 | 19.53 | 25.07 | 5.28 | 49.9 | 19.5 | 25.1 | 5.3 | 39.2 |
| 52 | AVCat116 | 17:30 | 56.61 | 59.94 | 2.29 | 9.77 | 28.00 | 40.1 | 2.3 | 9.8 | 28.0 | 5.7 |
| 53 | AVCat117 | 17:40 | 17.19 | 21.49 | 17.77 | 0.62 | 60.11 | 78.5 | 17.8 | 0.6 | 60.1 | 22.6 |
| 54 | AVCat118 | 17:50 | 76.56 | 61.17 | 22.08 | 13.86 | 2.89 | 38.8 | 22.1 | 13.9 | 2.9 | 56.9 |
| 55 | AVCat119 | 18:00 | 49.17 | 41.41 | 19.63 | 13.04 | 25.92 | 58.6 | 19.6 | 13.0 | 25.9 | 33.5 |
| 56 | AVCat120 | 18:10 | 88.57 | 70.87 | 25.36 | 1.95 | 1.82 | 29.1 | 25.4 | 2.0 | 1.6 | 87.0 |
| 57 | AVCat121 | 18:20 | 60.02 | 35.79 | 47.18 | 0.59 | 16.46 | 64.2 | 47.2 | 0.6 | 16.5 | 73.4 |
| 58 | AVCat122 | 18:30 | 48.46 | 37.34 | 15.84 | 31.16 | 15.66 | 62.7 | 15.8 | 31.2 | 15.7 | 25.3 |
| 59 | AVCat123 | 18:40 | 89.82 | 87.19 | 0.45 | 10.52 | 1.84 | 12.8 | 0.5 | 10.5 | 1.8 | 3.5 |
| 60 | AVCat124 | 18:50 | 52.77 | 48.31 | 10.80 | 16.52 | 22.37 | 51.7 | 10.8 | 18.5 | 22.4 | 20.9 |
| 61 | AVCat125 | 19:00 | 83.93 | 73.05 | 19.43 | 1.01 | 6.51 | 26.9 | 19.4 | 1.0 | 6.5 | 72.1 |
| 62 | AVCat126 | 19:10 | 61.73 | 35.29 | 36.92 | 26.64 | 1.15 | 64.7 | 36.9 | 26.6 | 1.1 | 57.1 |
| 63 | AVCat127 | 19:20 | 67.64 | 29.38 | 62.22 | 7.84 | 0.58 | 70.6 | 62.2 | 7.8 | 0.6 | 88.1 |
| 64 | none | 19:30 | 101.20 | 100.00 | 0.00 | 0.00 | 0.00 | 0.0 | 0.0 | 0.0 | 0.0 | |

What is claimed is:

1. A reactor assembly comprising:

at least one flow-through reactor for performing at least one chemical reaction, the flow-through reactor comprising:

a reaction chamber, comprising a reaction zone, the reaction chamber being connected to at least one reactor inlet for at least one reactant, upstream of the reaction zone, and to at least one reactor outlet for the effluent stream from the reaction zone, downstream of the reaction zone, at least one analyser for subjecting the effluent stream to an analysing procedure, each reactor outlet being connected to said at least one analyser by an effluent conduit, wherein the reactor assembly comprises:

at least one dilution fluid supply means, for adding at least one dilution liquid to the effluent stream, downstream of the reaction zone, a base block having a plurality of reactor chamber channels therein, each reactor chamber channel being accessible from a first face of the base block;

a releasable cover element that covers the first face of the base block in operation of the reactor assembly;

a plurality of tubular reaction chambers, each tubular reaction chamber having an inlet and an outlet at the opposite ends thereof, each tubular reaction chamber being accommodated within a corresponding reaction chamber channel of the base block and being removable therefrom;

the cover element being provided with a plurality of reactant feed channels each in communication with an inlet of a tubular reaction chamber;

a first sealing element being disposed between the first face of the base block and the cover at each first channel; and a second sealing element being disposed in the first channel between each tubular reaction chamber and the base block so as to separate an upstream portion of the reaction chamber channel in open communication with the reaction chamber inlet from a downstream portion of the reaction chamber channel in open communication with the reaction chamber outlet;

wherein for each reaction chamber channel an effluent channel is formed in the base block, which effluent channel extends from the downstream portion of reaction chamber channel to a second face of the base block; and wherein the reactor assembly further includes a plurality of diluent fluid supply channels, each in fluid communication with a downstream portion of a reaction chamber channel.

2. Reactor assembly for analysing the effluent stream from at least one flow-through reactor, comprising:

at least one flow-through reactor for performing at least one chemical reaction, the reactor comprising:

a reaction chamber, comprising a reaction zone, the reaction chamber being connected to at least one reactor inlet for at least one reactant, upstream of the reaction zone, at least one reactor outlet for the effluent stream from the reaction zone, downstream of the reaction zone, wherein the reactor assembly further comprises:

a feed conduit that is in fluid communication with the reactor inlet, upstream of the reaction zone, for feeding a reactant to the reaction chamber, an effluent conduit, which comprises an effluent conduit inlet and an effluent conduit outlet, wherein the effluent conduit inlet is in fluid communication with the reactor outlet, a gas/liquid separator, that has a gas/liquid separator inlet, a gas outlet and a liquid outlet, wherein the gas/liquid separator inlet is in fluid communication with the effluent conduit outlet, at least one analyser, for subjecting at least a part of the effluent to an analysing procedure, the analyser being arranged downstream of the gas/liquid separator, and at least one dilution liquid supply means, for adding at least one dilution liquid to the effluent stream, which dilution liquid supply means is in fluid communication with the reaction chamber or to the effluent conduit, wherein the connection of the dilution liquid supply means to the reaction chamber or to the effluent conduit is at a location downstream of the reaction zone and upstream of the gas/liquid separator.

3. Reactor assembly according to claim 2, wherein the dilution liquid supply means is connected to the reaction chamber or to the effluent conduit at a location which is at most 10 mm from the downstream end of the reaction zone.

4. Reactor assembly according to claim 2, wherein the analyser is in fluid communication with the gas outlet of the gas/liquid separator.

5. Reactor assembly according to claim 2, wherein the analyser is in fluid communication with the liquid outlet of the gas/liquid separator.

6. Reactor assembly according to claim 2, wherein the reactor assembly further comprises a sample collection system for receiving effluent from the gas outlet and/or liquid outlet of the gas/liquid separator.

7. Reactor assembly according to claim 2, wherein the dilution liquid supply means comprises flow rate control means, which flow rate control means are set such that the ratio in the diluted effluent stream, between volumetric diluent liquid flow:

volumetric reactor liquid effluent flow is 0.2-10000:1, more preferably 1-1000:1 and most preferably 10-100:1.

* * * * *

UNITED STATES PATENT AND TRADEMARK OFFICE
CERTIFICATE OF CORRECTION

PATENT NO. : 7,625,526 B2 Page 1 of 1
APPLICATION NO. : 10/477028
DATED : December 1, 2009
INVENTOR(S) : van den Brink et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1272 days.

Signed and Sealed this

Twenty-first Day of December, 2010

David J. Kappos
*Director of the United States Patent and Trademark Office*